(12) United States Patent
Accardo et al.

(10) Patent No.: US 10,123,795 B2
(45) Date of Patent: Nov. 13, 2018

(54) MINIMALLY INVASIVE SURGICAL TECHNIQUE TO PERFORM VAGINAL OSTIOPLASTIC AND ANUS TIGHTENING

(71) Applicant: PROMOITALIA GROUP S.p.A., Milan (IT)

(72) Inventors: Ciro Accardo, Portici (IT); Valerio Matano', Naples (IT); Egidio Tranfaglia, Naples (IT)

(73) Assignee: PROMOITALIA GROUP S.P.A., Milan (IT)

( * ) Notice: Subject to any disclaimer, the term of this patent is extended or adjusted under 35 U.S.C. 154(b) by 616 days.

(21) Appl. No.: 14/518,065

(22) Filed: Oct. 20, 2014

(65) Prior Publication Data

US 2016/0106410 A1   Apr. 21, 2016

(51) Int. Cl.
| | |
|---|---|
| *A61B 17/04* | (2006.01) |
| *A61L 17/00* | (2006.01) |
| *A61B 17/06* | (2006.01) |
| *A61B 17/00* | (2006.01) |

(52) U.S. Cl.
CPC ............ *A61B 17/06166* (2013.01); *A61B 2017/00792* (2013.01); *A61B 2017/00805* (2013.01); *A61B 2017/06176* (2013.01)

(58) Field of Classification Search
CPC .... A61B 17/06166; A61B 2017/06176; A61B 2017/1142

USPC .................................................. 606/144–148
See application file for complete search history.

(56) References Cited

U.S. PATENT DOCUMENTS

2003/0074023 A1* 4/2003 Kaplan ............ A61B 17/00234
606/228

* cited by examiner

*Primary Examiner* — Elizabeth Houston
*Assistant Examiner* — Lindsey Bachman
(74) *Attorney, Agent, or Firm* — Young & Thompson

(57) ABSTRACT

A method to perform mini-invasive vaginal ostium plastic surgery and anal tightening procedures, includes:
- using at least one barbed cylindrical suture with barbs divided into two divergent groups, the sharp ends of the barbs being inclined in the direction of the respective ends, so as to oppose the traction of the thread exerted on both ends, each end being provided with a needle;
- preparing insertion and emergence cuts in the working plane of the female perineum;
- introducing the barbed suture thread by inserting needles placed at its ends, at different times, into the same starting hole, in order to emerge from the same outlet hole, thus completing the path in different anatomical planes of the female perineum;
- tying together the two ends of the at least one suture after having emerged from the same outlet hole, then closing the loop with at least one knot.

6 Claims, 47 Drawing Sheets
(45 of 47 Drawing Sheet(s) Filed in Color)

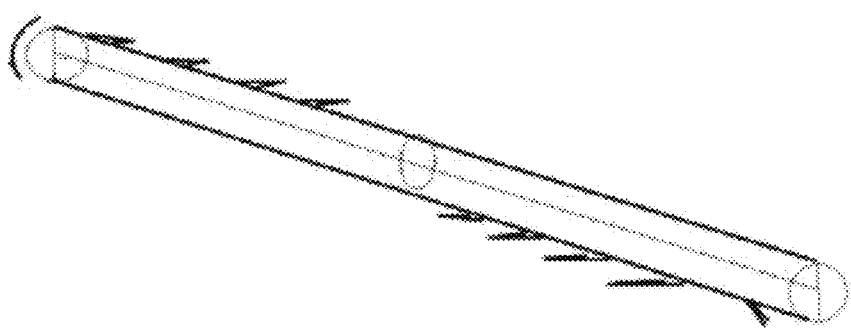
Fig. 2b
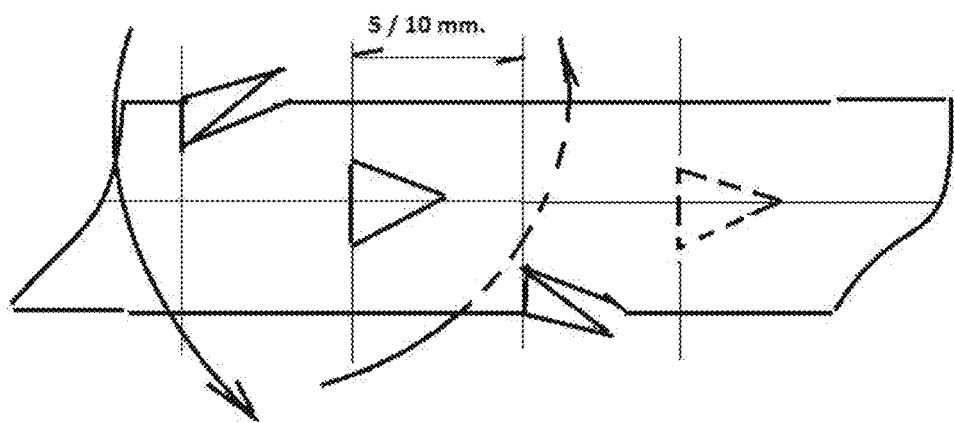
Fig. 2
Fig. 2c

Introduction of the anoscope and evaluation of the anatomical layers of the urogenital and anal triangle Indications of reference points and indications of entry and exit holes of the barbed sutures Topical and/or troncular anesthesia of the lumbosacral nerve plexus Fig. 35 Cutaneous incision with a dermal punch having a 2 mm diameter Fig. 37 Insertion of the suture or sutures according to the path already illustrated Insertion of the suture or sutures according to the path already illustrated Fig. 42 — Tension of the latter once the last exit hole has been reached, and securing the latter with a knot Tension of the latter once the last exit hole has been reached, and securing the latter with a knot Tension of the latter once the last exit hole has been reached, and securing the latter with a knot Tension of the latter once the last exit hole has been reached, and securing the latter with a knot Fig. 46 Tension of the latter once the last exit hole has been reached, and securing the latter with a knot

MINIMALLY INVASIVE SURGICAL TECHNIQUE TO PERFORM VAGINAL OSTIOPLASTIC AND ANUS TIGHTENING

The present invention relates to medicine, specifically to methods for performing general and specialized surgery, plastic surgery, cosmetic and dermatologic surgery, gynecologic and/or obstetric surgery, and/or andrological surgery for "Anal Tightening". In particular, the present invention relates to the use of medical materials used as fillers or repositioning or sealing means, or lifting, aggregation, compaction or tightening means for skin, subcutaneous tissue, muscles, tendons or connective fasciae.

FIELD OF THE INVENTION

The female pelvic floor consists of voluntary muscles, fascia and ligaments. These structures have a support component and a functional component. They support bladder, vagina, uterus and rectosigmoid, and are involved in bladder emptying and continence. They are also involved in providing the vaginal wall and uterine cervix, and the uterus with a supporting function, and also act in the normal accomplishment of sexual function. They further have a very important role in defecation and fecal continence. Abnormalities of the pelvic floor result in the incurrence of urinary incontinence, uterovaginal prolapse, sexual dysfunctions, and inability to defecate or fecal incontinence.

Because of individual factors, each of the methods of vaginal tightening suggested in the present patent will not be exactly the same, and this is in connection with the different clinical conditions experienced by each specific patient. The clinician will choose the most suitable surgery from those suggested in this patent, giving priority to the insertion of a suture thread, one of the techniques disclosed which involve a path consisting of a single loop and/or a double and/or triple loop and/or a quadruple loop (where the loop can be ring-shaped, triangular, quadrilateral-shaped or polyhedron-shaped).

Surgical complications which may occur include hematoma, infections and reactions to drugs for anesthesia. Before and after surgery, the tips and instructions provided in advance by the practitioner should be followed, thus reducing much of the risk. In any case, complications are incomparably more rare with respect to classical or traditional surgery.

It is worth noting that the effectiveness of the surgical technique being described is linked to the outcome of the vaginal tightening or narrowing which may be considerable but, though in rare cases, such a technique can only give minor improvements, because the result depends on the degree of pre-intervention relaxation of the perineal and vaginal muscles, on the age of the patient, the traumas suffered, the number of pregnancies completed, etc. Also, we must here reiterate that the vaginal, vulvar and perineal tightening can improve or solve the relaxation and/or hypotonia of the muscles of the aforementioned anatomical area, but cannot address and/or solve the psychological aspects related to the female sexuality which are attributable to psychology.

Some women after childbirth warn very often a feeling of vaginal relaxation due to the fact that during the delivery the head of the fetus was too big, which could lead to the consequent thinning of the vaginal wall and/or to muscle tears. Sometimes, in order to facilitate the release of the baby from the birth canal, especially when there are clinical signs of fetal distress, episiotomy is used, i.e. a surgical procedure consisting of a surgical cutting (tomy) of the perineum (episeion, pubic region) laterally with respect to the vagina, to widen the birth canal, and often such a cut is not properly sutured by the practitioner or the midwife operator who oversees the delivery, thus resulting in pelvic prolapse, reduction in contractile strength of the vaginal muscles, and therefore decreased or absent sexual pleasure during sexual activity later. Pregnant women do not usually pay any attention to prenatal training and vaginal gym (vaginal exercises, otherwise known as Kegel exercises), which stimulate the muscles of the perineum involved in the childbirth while leading them to hypertrophy. This lack of adequate preparation for future birth will result in a higher risk of incurring in the above-mentioned traumas.

Despite these criticalities, the vaginal tightening being described arises as a novel technique to solve the physiological changes which women are likely to experience, in order to improve the quality of couple life.

OBJECTS OF THE INVENTION

It is a first object of the surgical technique of the present invention to solve or improve the vaginal laxity, the hypotonicity of the female perineum upon general traumas and/or physiological birth traumas and/or iatrogenic traumas, i.e. caused by the practitioner, such as for example the above-mentioned episiotomy and/or poorly executed plastic surgery on the female perineum, which involve the surface and deep anatomical planes of the aforementioned area.

It is a second object of the invention to suggest an innovative method which allows to solve the muscle hypotonicity and skin laxity due to female hormone climate changes after menopause, and also to take care of the external anal sphincter hypotonia.

It is a third object of the invention to provide a surgical technique which allows to reduce and/or contract the size of the vaginal ostium (opening) and/or of the vagina, or to reduce the dilation or prolapse of the external anal sphincter.

With a more appropriate and specific terminology, the technique of the invention and, in general, the surgery that we suggest can be defined as "minimally invasive Perineum Raffia" and "minimally invasive vaginal ostium plastic surgery" and "vaginal tightening".

According to a peculiar feature of the invention, a barbed suture thread is used, with micro barbs or notches on the surface, which represents an improvement of the suture subject of the International Patent Application No. WO 2006/061868, filed by the same Applicant. In such an application, protrusions or barbs were expected to be made on the outer surface of the suture, being properly sloped and arranged in sequences with the tips converging or diverging with respect to the midpoint of the suture or to the midpoint of the length of a repeating unit, and said barbs were also expected to be distributed on the suture in the form of a spiral.

The innovative feature of the barbed suture which is used in the present invention is that each barb obtained on the suture itself has three orders of engraving or carving, where the values of the cutting angles, corresponding to those of the cutting blade, are chosen in a range from a minimum value of 3° to a maximum value of 87° or a maximum value of 177° and a minimum value of 93° (geometrically complementary).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The detailed description of the surgical method according to the present invention and the specific features of the suture used will become more apparent with reference to the accompanying drawings, in which:

FIG. 2b shows another cylindrical section suture thread, with bidirectional protrusions or barbs or notches again located on two diametrically opposed generatrices of the suture, but converging to the midpoint;

FIG. 2c shows a right-handed or left-handed rotating spiral with a pitch comprised from 5 to 10 mm, and step-wise advancement in the spiral-development direction of 90° degree.

FIG. 26 shows the materials and tools needed for the technique described;

FIG. 27 is an external view of female perineum;

FIG. 28 shows the surface muscle planes of the female perineum;

FIG. 29 shows the sterilization step;

FIG. 30 shows the catheterization step;

FIG. 31 shows the step of introducing an anoscope for the evaluation of the anatomical planes and for the evaluation of the reference points for the surgery;

FIG. 32 is a front view showing the reference points to achieve skin cuts;

FIG. 33 is an oblique view showing the reference points to achieve skin cuts;

FIG. 34 shows the step of topical and nerve block anesthesia of the lumbosacral plexus;

FIG. 35 shows the skin cuts made in the reference points with a derma punch having a diameter of 2 mm;

FIG. 36 shows the removal of dermal dissection cylinders, having a diameter of 2 mm;

FIG. 37 shows the insertion of the right suture half-length, from the cut or cranial cut located on the central axis;

FIG. 38 shows the emergence of the suture according to the invention on the right internal transverse cut located on the projection of the transverse muscle of the perineum;

FIG. 39 shows the introduction of the vaginal suture on the same right internal transverse cut;

FIG. 40 shows the emergence of the needle of the vaginal suture on the median distal cut, located on the median raphe (body of the perineum);

FIG. 41 shows the complete emergence of the vaginal suture on the median distal cut, located on the median raphe (body of the perineum);

FIG. 42 shows the insertion of the left suture half-length, from the same cut or cranial cut located on the median axis;

FIG. 43 shows the emergence of the vaginal suture on the left internal transverse cut located on the ipsilateral projection of the transverse muscle of the perineum;

FIG. 44 shows the introduction of the vaginal suture on the same left internal transverse cut;

FIG. 45 shows the complete emergence of the vaginal suture needle on the median distal cut located on the median raphe (body of the perineum);

DETAILED DESCRIPTION OF THE INVENTION

Figure 1:
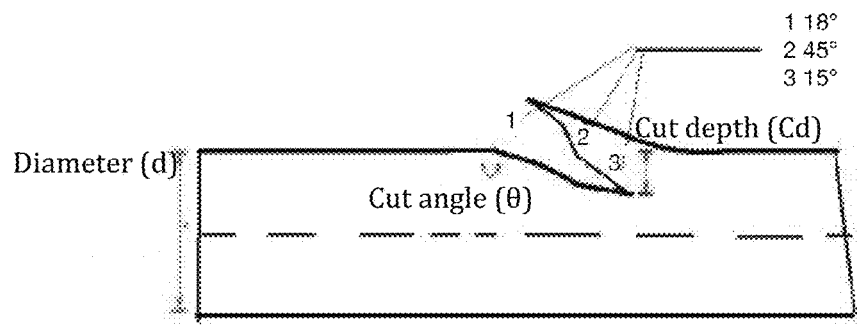
FIG. 1 is a suture detail showing a barb obtained by three orders of notches made on the outer surface.
Figure 2A:
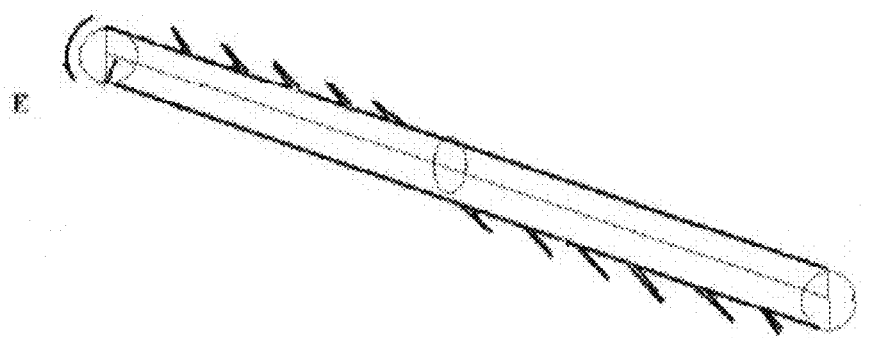
FIG. 2a shows a perspective view a cylindrical section suture thread with bidirectional protrusions or barbs or notches diverging from a midpoint, which are located on two diametrically opposite generatrices of the suture.
Figure 3:
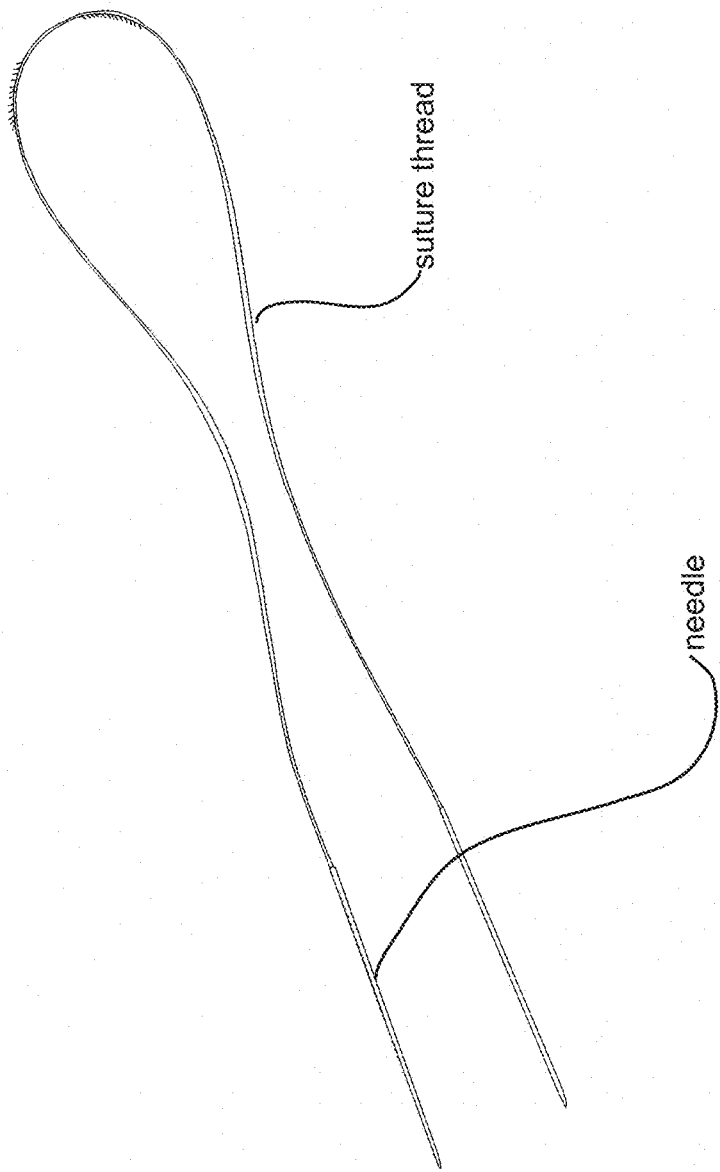
FIG. 3 diagrammatically depicts, not in scale, the vaginal suture provided with barbs with a needle at each end.

As already mentioned, the vaginal surgical technique described includes the use of a barbed suture thread which was the subject of the International Patent Application No. WO 2006/061868. As seen in FIGS. 2a and 2b, the micro-barbs or protrusions which cover in sequence the surface of such a suture thread are divided, with respect to the midpoint of the length of the suture itself, in two opposing groups which are convergent or divergent to each other depending on whether the pointed ends of the micro-barbs of the two center lines are inclined in the direction of said midpoint or in the direction of the respective ends. These may have overall lengths from 7 cm to 57 cm maximum. It should be noted that the converging barbs are not arranged on the same axis, but are out of phase of 90° (FIG. 1), i.e. arranged in their sequence and spatial development, so as to be along four generatrices angularly spaced apart of 90° with snapped helical development of 90° and feeding pitch from 0.5 to 10 mm, from the midpoint to the right and left ends, respectively (FIG. 2).

The gauge of the sutures specifically used for vaginal, vulvar, perineal and vaginal ostium tightening is in the range of 4 USP, 2 USP, 1 USP, 0 USP, 1/0 USP, 2/0 USP, 3/0 USP, 4/0 USP.

United States Pharmacopeia is the standard nomenclature which regulates tolerances and specifications of permanent and absorbed sutures in the US.

The threads are made of polypropylene or caprolactone or polydioxanone or of another biocompatible or even inert material (e.g. silicone, etc.), but they can also be made of other kinds of materials, in particular mono- or multi-thread materials, with sharp or differently shaped protrusions, produced during the manufacturing process, arranged as a spiral with advancement shifting according to the major axis of the suture, snapped by 90° according to the specific pitch chosen in the range indicated above (see FIG. 2).

The new surgical techniques for the introduction of the specifically gauged suture for the innovative techniques mentioned below and the particular shape of the thread which allow the same suture thread to be introduced by using the technique of the single and/or double and/or triple and/or quadruple loop (the loop can be ring-shaped, triangular, quadrilateral-shaped or polyhedron-shaped, and with minor axis oriented parallel to the median line which centrally crosses the Rafe of the perineum (Perineal Body), while the longest axis is orthogonal to the former, see FIGS. 3-25.

Indeed, according to the invention, in the single loop, the two needles are inserted at different times, in the same starting hole, and emerge from the same outlet hole. However, the respective paths are completed in different planes, for example, the first in the superficial transverse muscle and the second in the deep transverse muscle, to then be tied together after being emerged from the same outlet hole. The technique can be applied both to the right and left side of the female perineum: this will depend on the place where the previous episiotomy was made.

Depending on the specific anatomical situation encountered in the vaginal, vulvar and perineal areas and in the anatomical planes to be anastomosed, the shape of the loop to be used (ring-shaped or triangular or sometimes polyhedron-shaped (pentagonal, hexagonal, etc.)) will be chosen by the operator. The loop is then closed and locked with a simple forehand, backhand suture knot or with multiple knots.

The surgical technique described has the great advantage (over the already ascertained techniques of conventional surgery, which are not free from significant post-surgical complications and long postoperative recovery) of reducing the duration of the surgery, reducing or eliminating the stay in the clinic (which extends for 2 hours, rarely with inpatient night), and reducing the period of postoperative rehabilitation, thus allowing an immediate return to the normal social and couple life.

Such a technique takes full advantage of the sharp serrations or projections, which are provided on the suture thread, giving the soft tissues, the corpora cavernosa and the muscle bundles of the different vaginal, vulvar and perineal planes—crossed during their introduction—aggregation and support in a very specific direction.

Moreover, due to the specific geometry thereof, the sutures show an action of revitalization of the subdermal matrix and of the muscle planes crossed, as documented by several scientific publications and, last but not least, ensure anchorage, tightening and sealing of soft tissues and/or fasciae, and/or planes crossed, over the whole development or elongation (path) of the vaginal barbed suture.

The insertion of the thread(s) used in the technical specification, according to the paths indicated above in relation to FIGS. 3-25, give rise to a powerful action of end-to-end adhesion of the superficial and deep muscles of the female perineum, in all cases in which these are torn by external trauma or upon physiological childbirth as well as episiotomy surgery in order to facilitate the delivery of the fetus. Moreover, similar surgeries can be used to solve the prolapse of the pelvic floor, i.e. for lifting and repositioning it, thus restoring its normal tonicity. The muscles are put back in their correct anatomical position, while restoring the existing anatomical situation.

Operating Procedure

Figure 4:
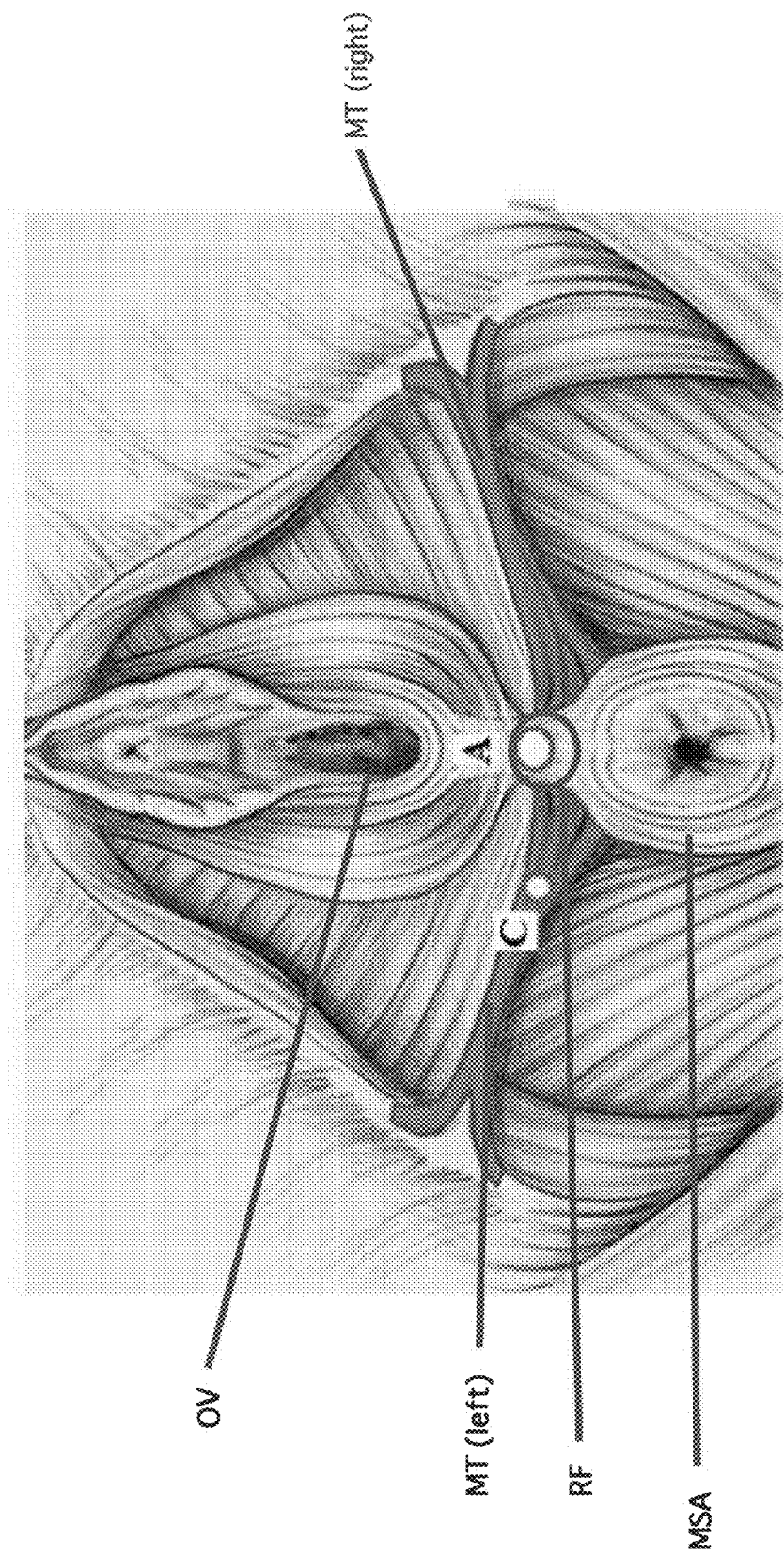
FIG. 4 is an anatomical view of the working plane of the female perineum in which the insertion cuts for the right loop technique are shown.

By way of example, FIG. 4 describes the anatomy of the working plane. OV denotes the vaginal ostium, RF the median raphe (perineal central body), MT the superficial transverse muscle of the female perineum (left side and right side) and MSA the muscle of the anal sphincter.

Figure 5:
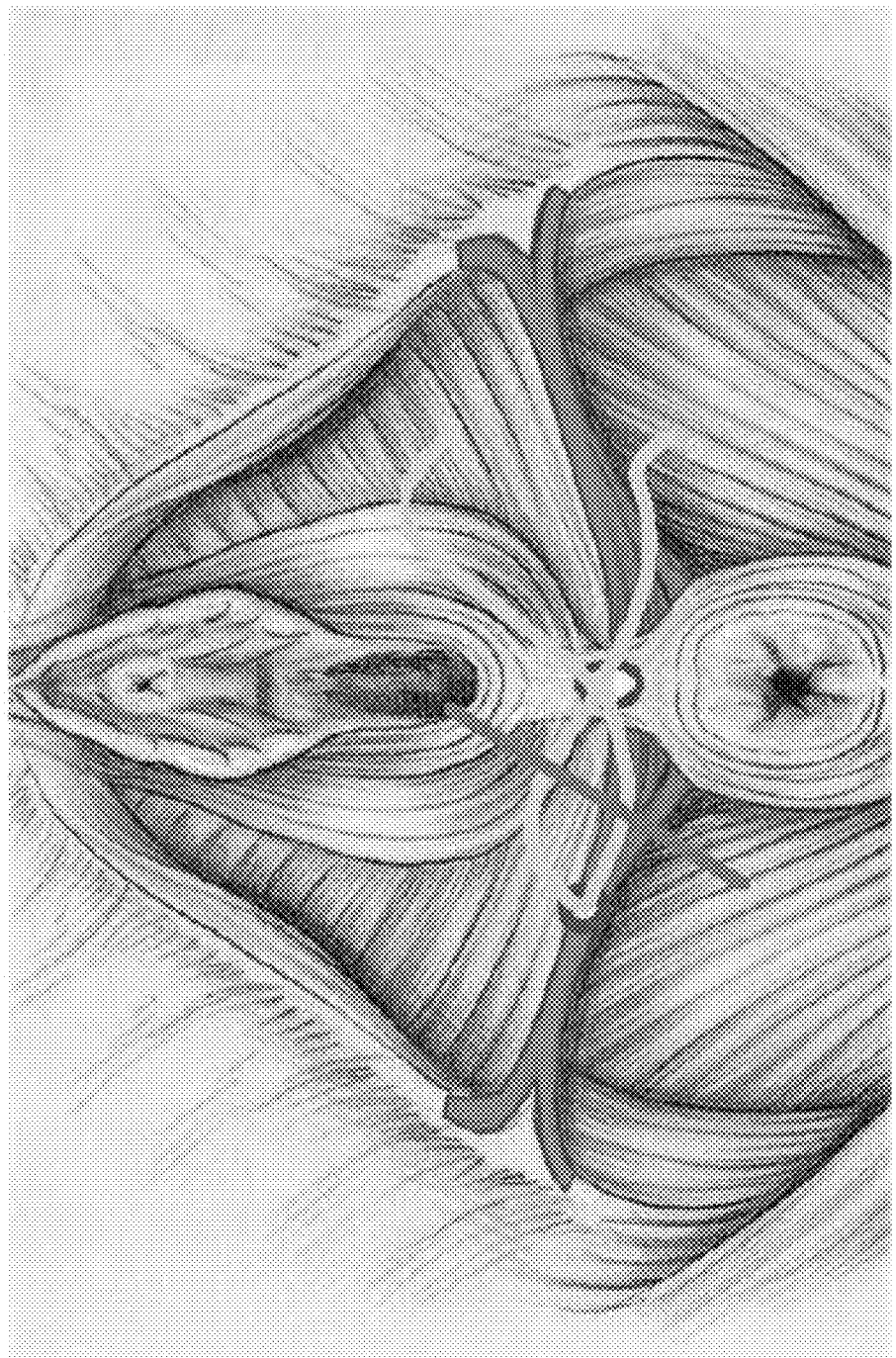
FIG. 5 shows the insertion paths of the thread, occurring with the right single loop technique.

In order to carry out a right loop technique, as the procedure is that shown in FIGS. 4 and 5.

Firstly, with a dermal punch of 2/2.5 mm, an initial cut A is made at the median raphe or perineal central body RF, almost at the lower fork of the vaginal ostium, and a second cut C is made, located on the right superficial transverse muscle MT. The two right and left needles at the ends of the single suture can be introduced either starting from cut A or from cut C and then emerge from cut C or cut A.

Figure 11:
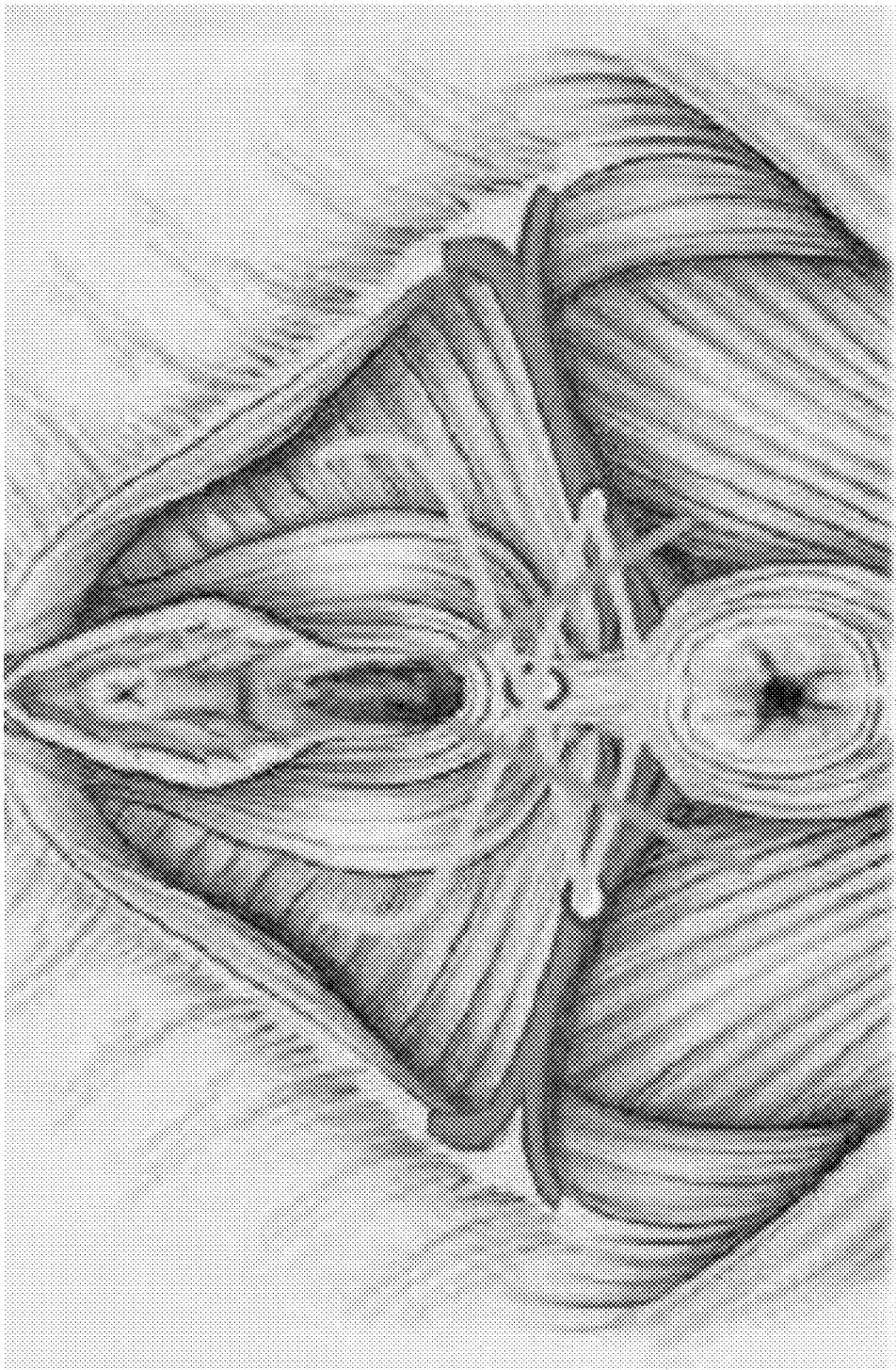
FIG. 11 shows the insertion paths of a thread using the triangular single loop technique with cranial knot.
Figure 12:
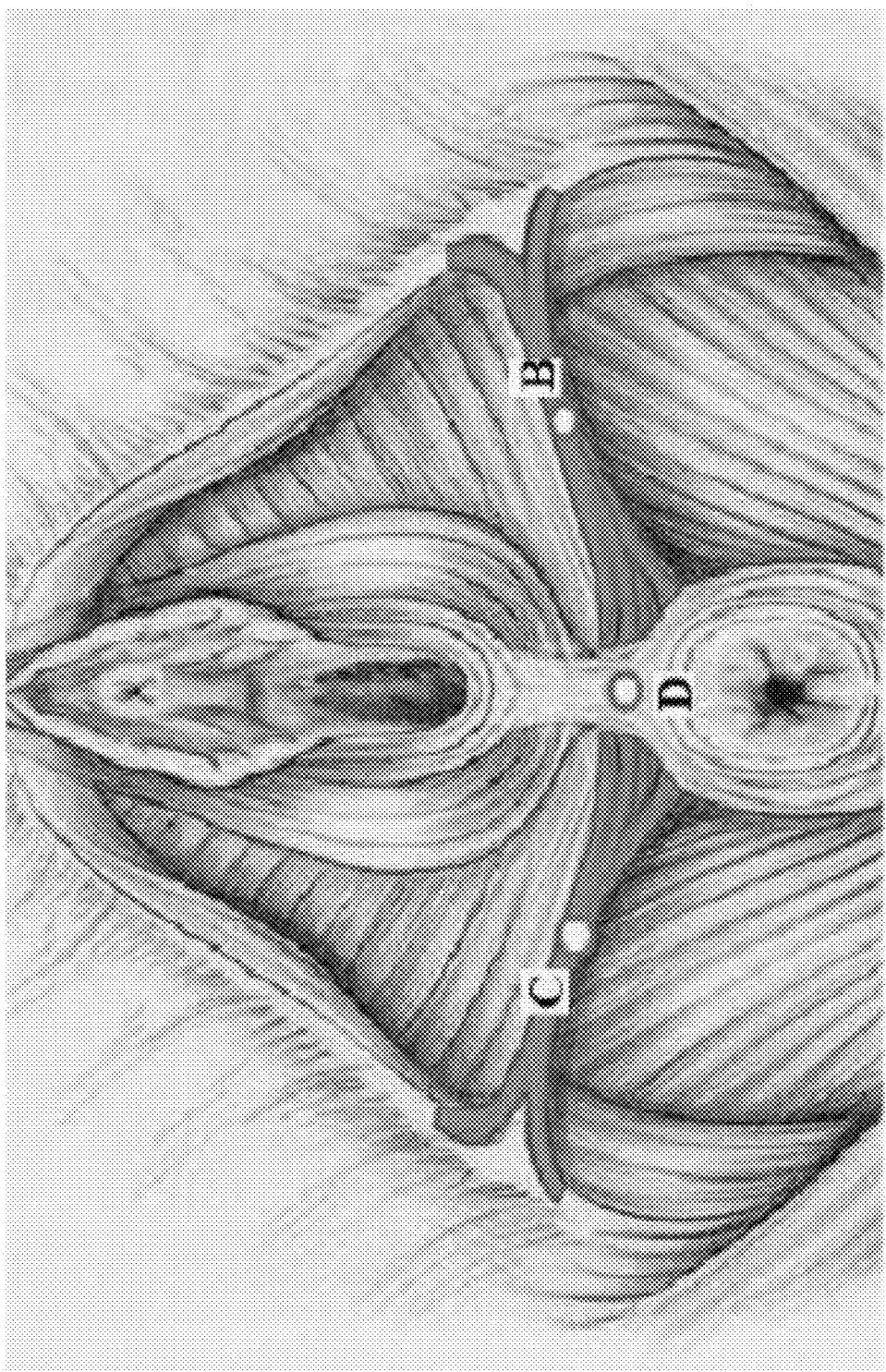
FIG. 12 is an anatomical view of the working plane where the insertion cuts for the triangular loop technique with knotted caudal cut are highlighted.
Figure 13:
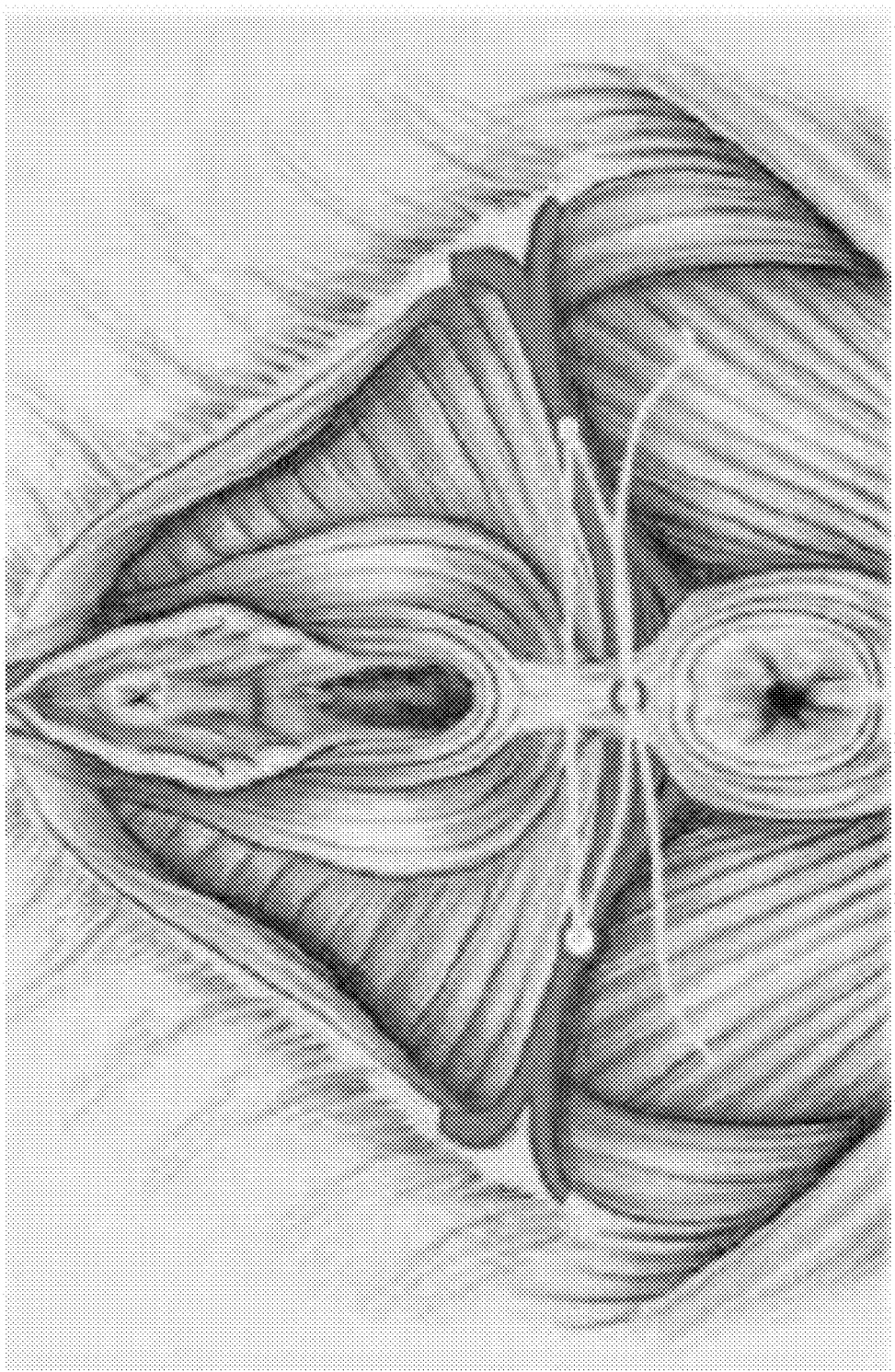
FIG. 13 shows the insertion paths of the thread used with the triangular single loop technique with caudal knot.
Figure 14:
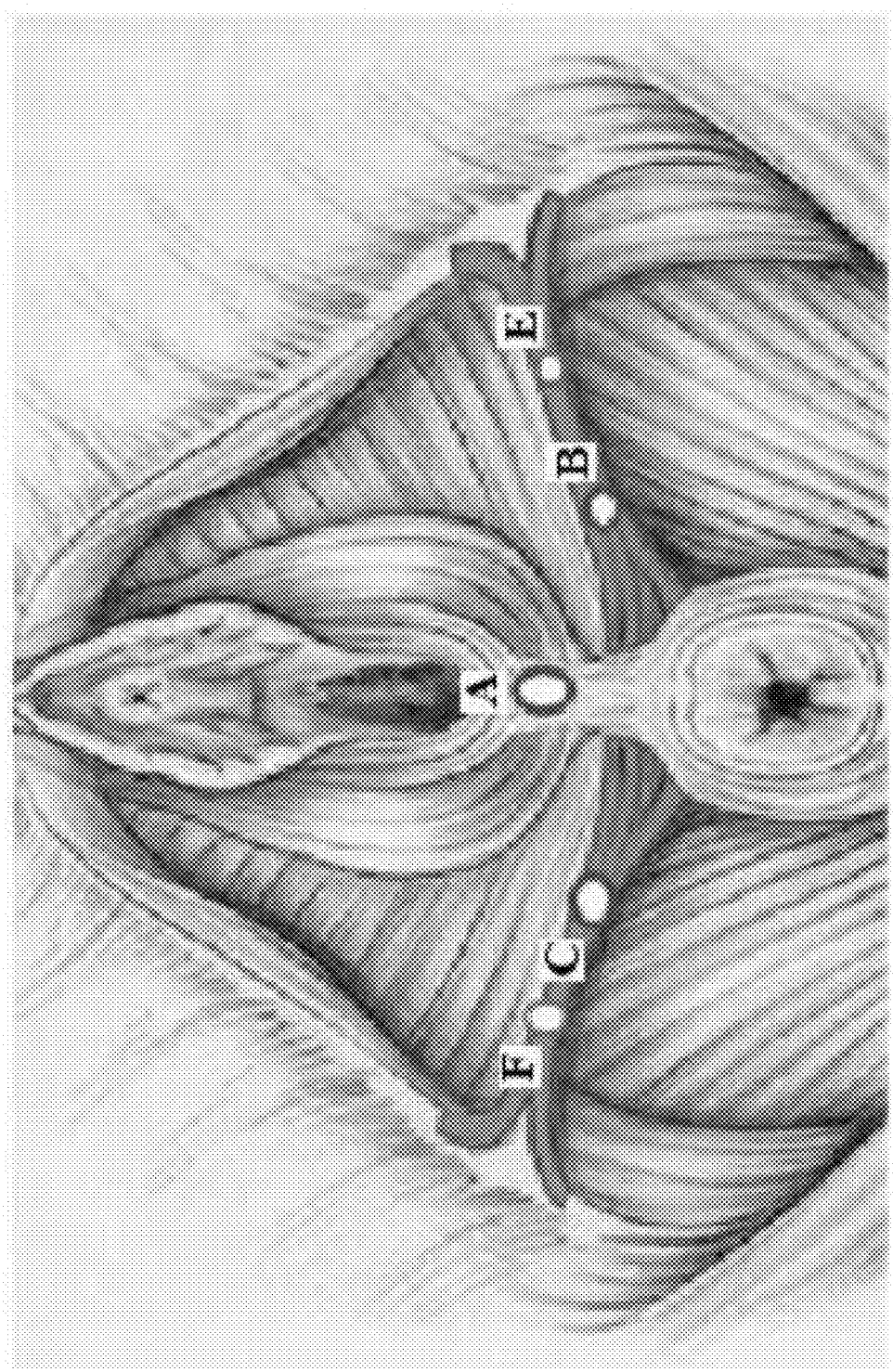
FIG. 14 is an anatomical view of the working plane where the insertion cuts for the triangular double loop technique with knotted cranial cut are highlighted.
Figure 15:
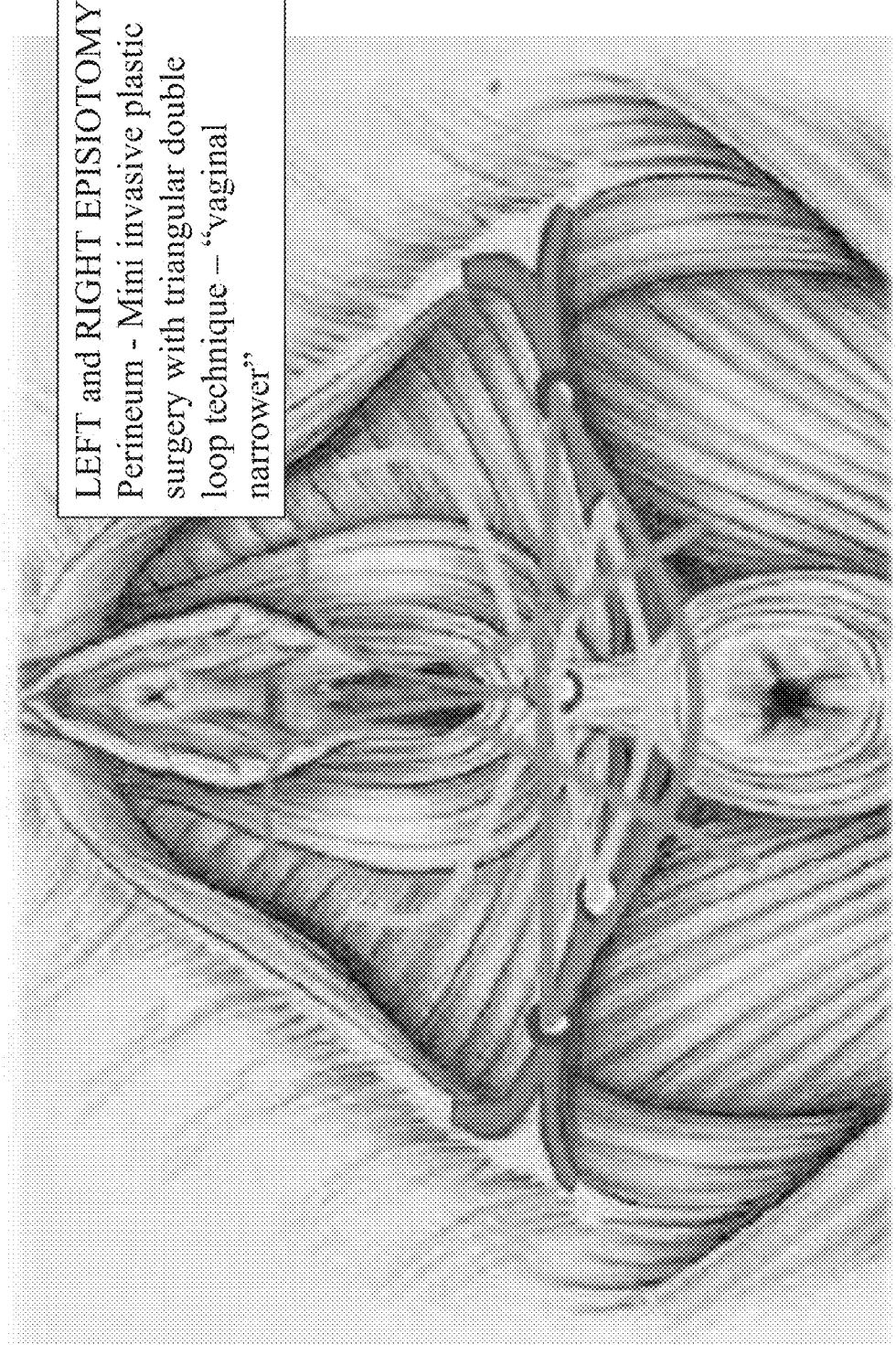
FIG. 15 shows the insertion paths of the two threads used for the triangular double loop technique with cranial knot.
Figure 16:
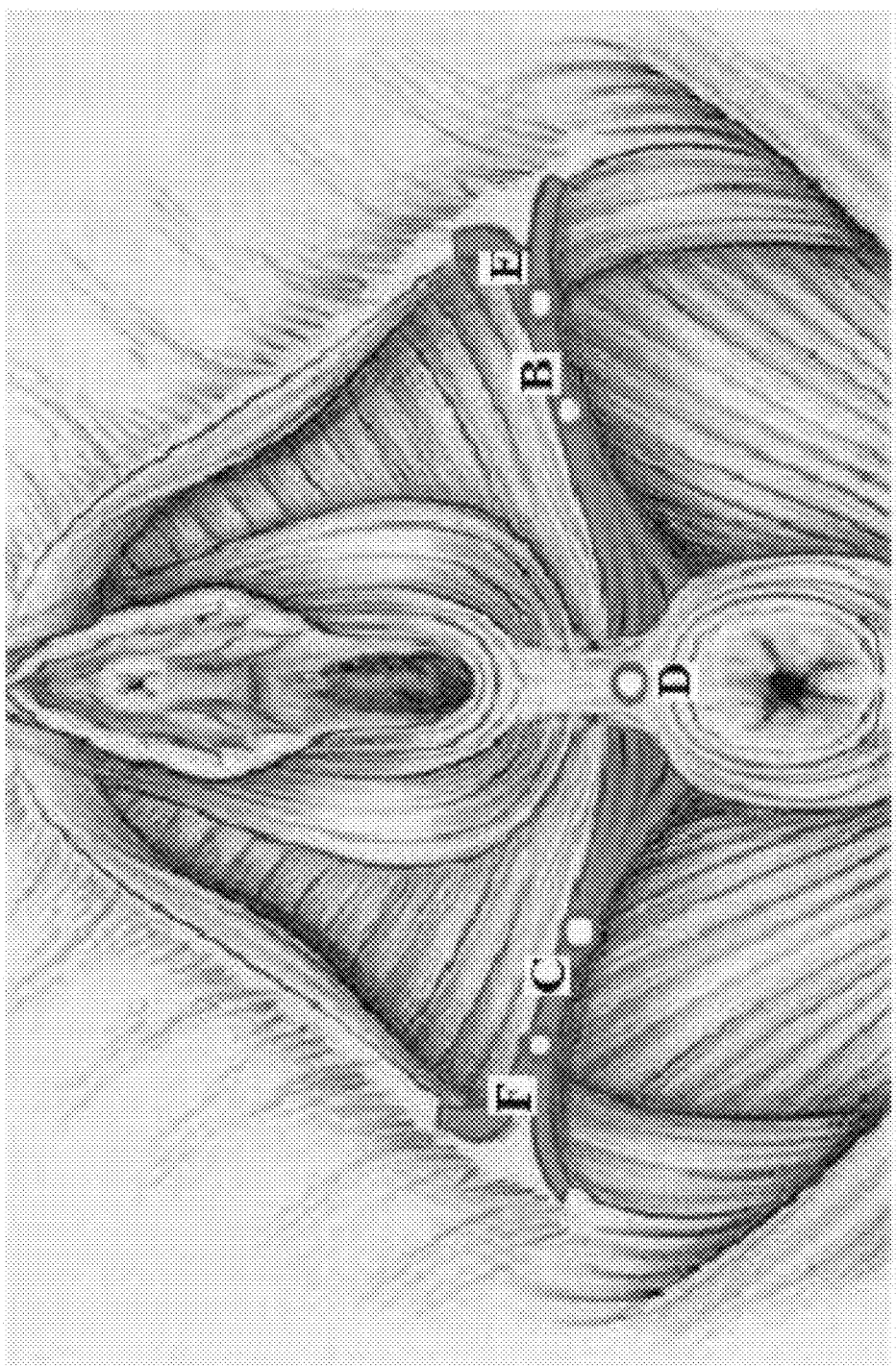
FIG. 16 is an anatomical view of the working plane where the insertion cuts for the triangular double loop technique with knotted caudal cut are highlighted.
Figure 17:
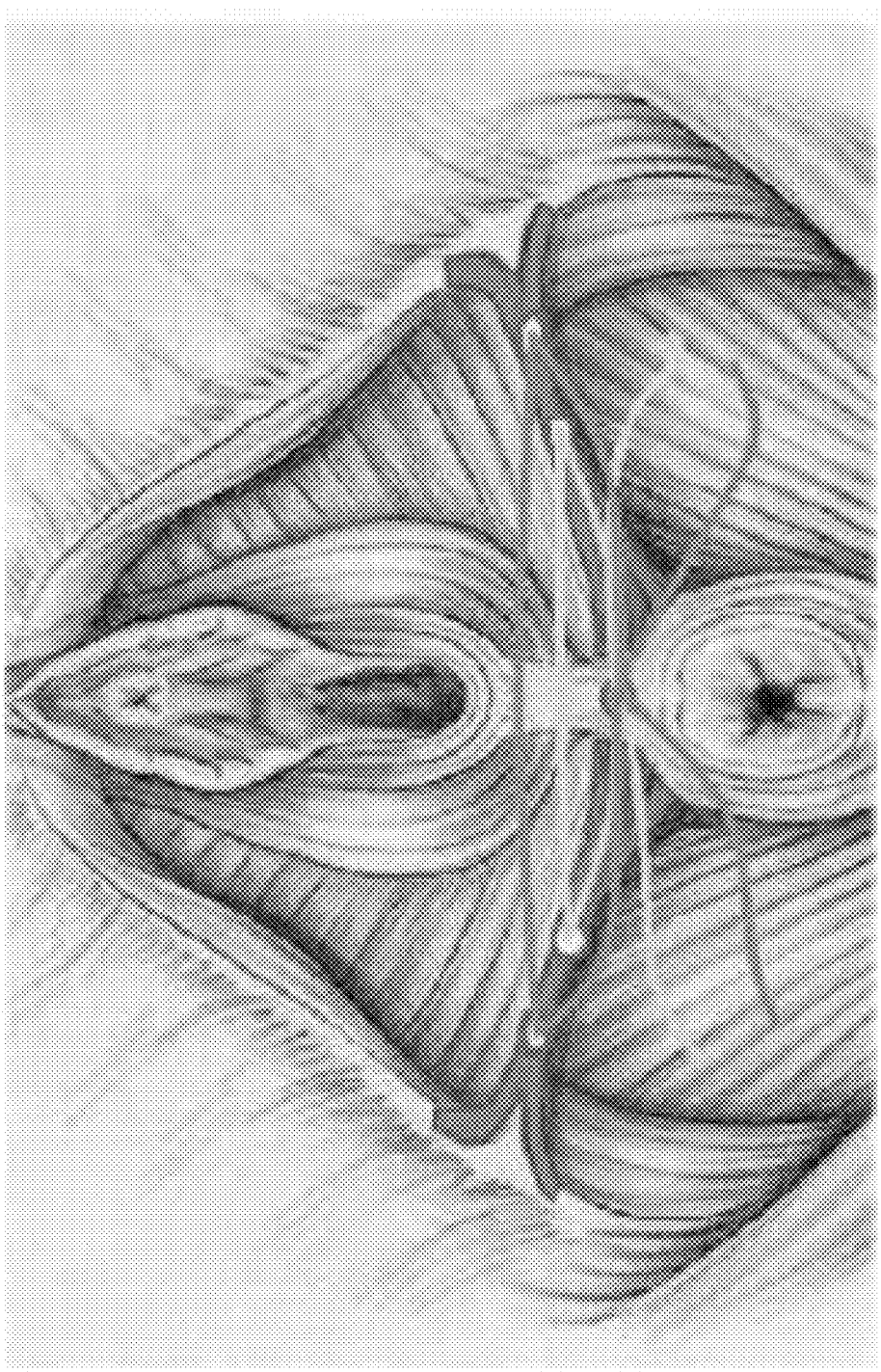
FIG. 17 shows the insertion paths of the threads used with the triangular double loop technique with caudal knot.
Figure 18:
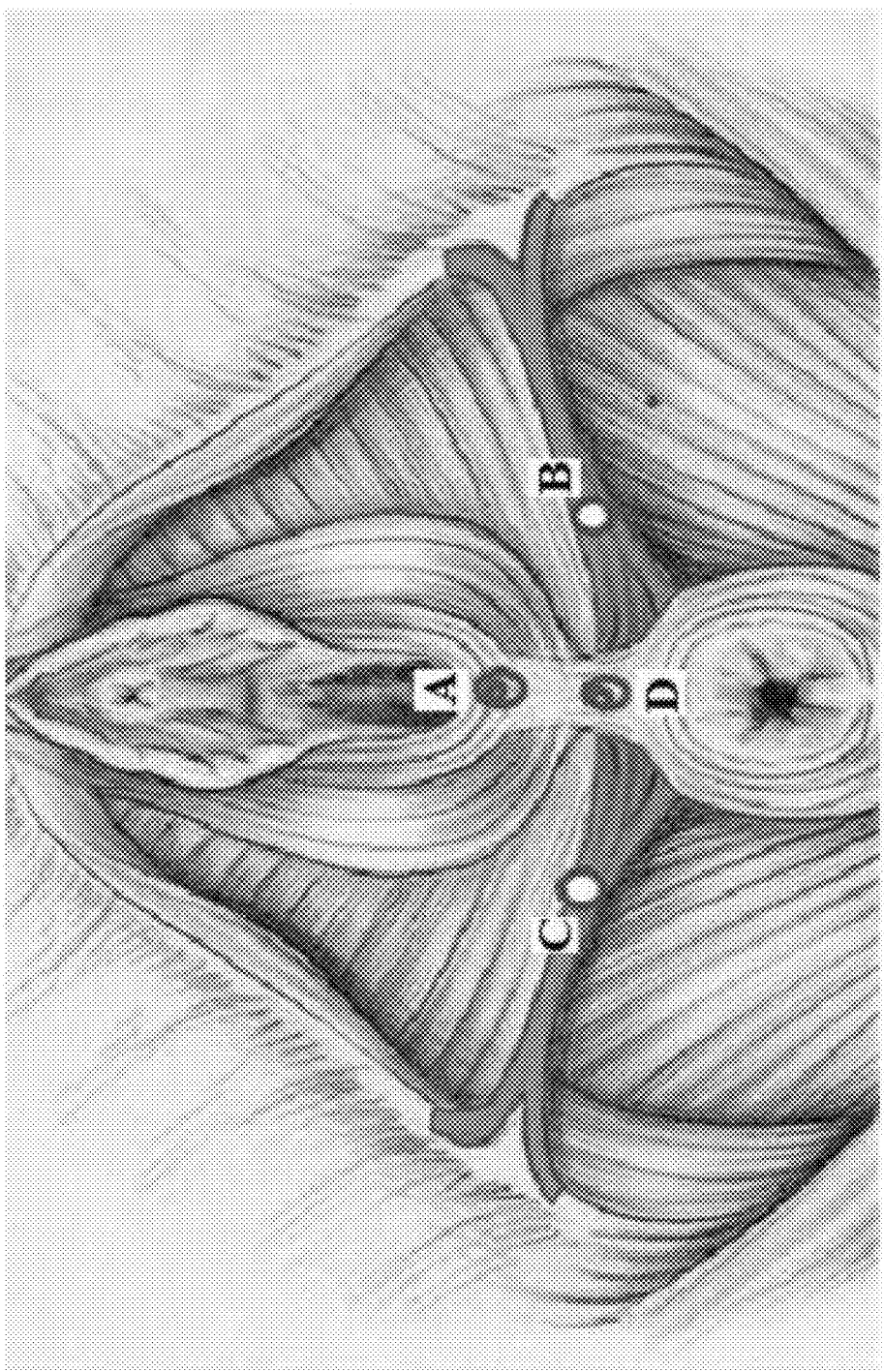
FIG. 18 is an anatomical view of the working plane where the insertion cuts for the quadrangular loop technique with knotted cranial and/or caudal cut are highlighted.
Figure 19:
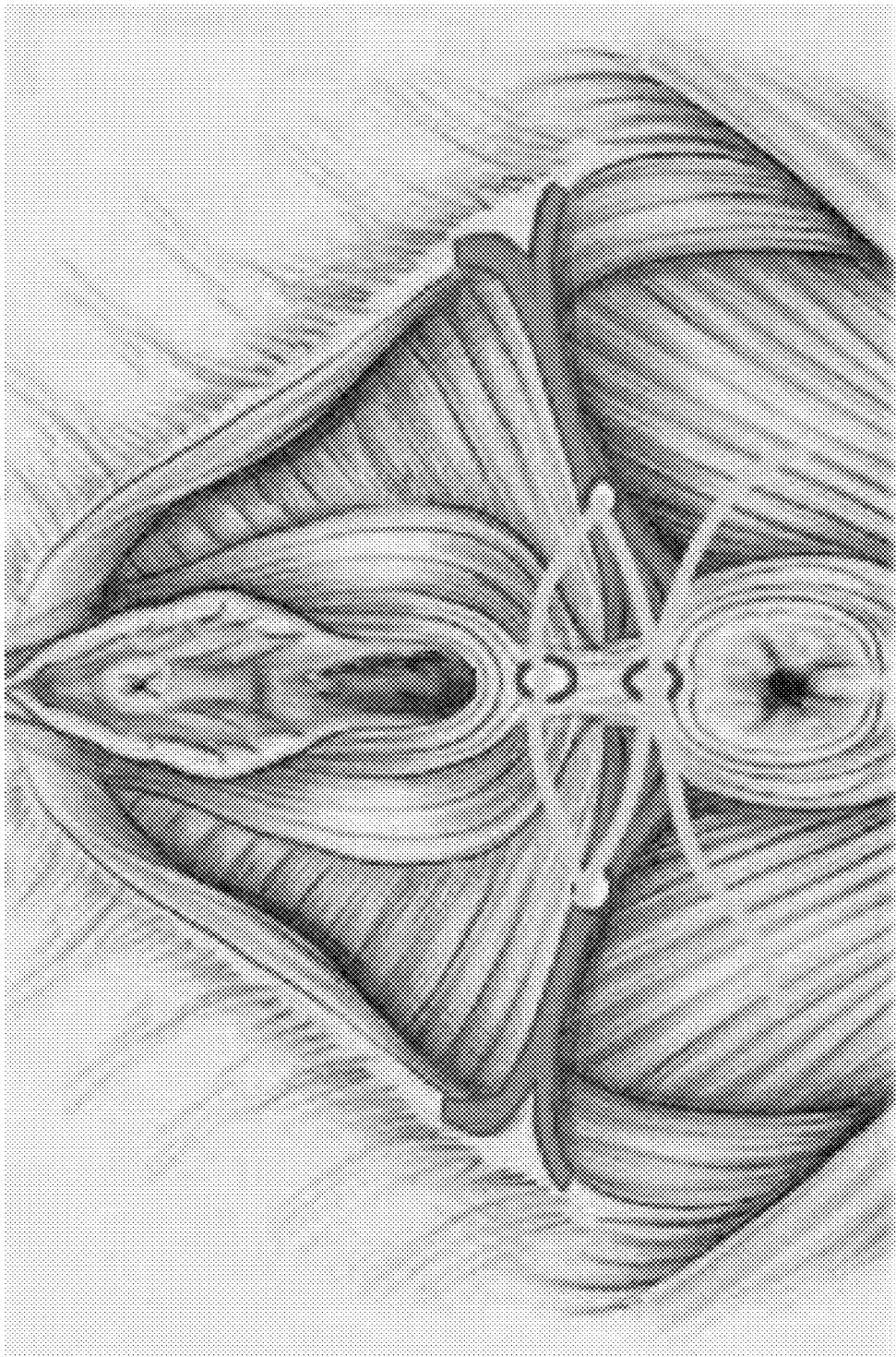
FIG. 19 shows the insertion paths of the thread used with the quadrangular loop technique with caudal knot.

In the hypodermis, the right needle mounted on a needle-holder will follow the right half-path of the simple loop, as shown in FIG. 5, of the triangular loop as seen in FIG. 11, the quadrangular diamond loop as shown in FIG. 18 or of the polyhedron-shaped loop placed on the median raphe, see FIGS. 22 and 37, 38, 39 and 40, while the other left needle will follow the left half-way as shown in the same FIGS. 5, 11, 18, 22, as well as in FIGS. 42, 43, 44 and 45, up to exactly placing the midpoint of the suture thread at the cranial median starting point, in this case point A.

The size of the needle ranges from 5 cm to 15 cm in length with a gauge from 24 to 18 gauge.

The needles will follow the paths indicated in the figures from FIG. 37 to FIG. 45 and from FIG. 4 to FIG. 24, respectively, up to emerge from the caudal sagittal median hole placed at about ½ cm, located again on the median raphe but more distally. Once the loop is made, it will be tightened with a forehand, backhand, forehand, or multiple suture knot.

The second loop, if required, will be introduced from the caudal hole D or F (see the figures cited above), also located on the median raphe up to reach with the same method the cranial median hole A, but through the right and left external transverse holes as shown in the accompanying drawings. Where necessary, the second loop which is longer and includes the first loop, will be also tightened with a forehand, backhand, forehand, multiple suture knot For a better understanding of the invention, we analyze the technique employed in the specific cases shown by way of example in FIGS. 3 to 25.

The first example illustrated in FIGS. 4 and 5 concerns a left mini-invasive episiotomy plastic surgery with a single suture. The technique used is that of the right single loop.

The suture can be introduced from cut A or C indifferently. The two right and left needles are introduced from cut A or cut C, emerging from cut C or A, as an outlet hole, where a multiple, forehand, backhand or single simple knot is made.

Figure 6:
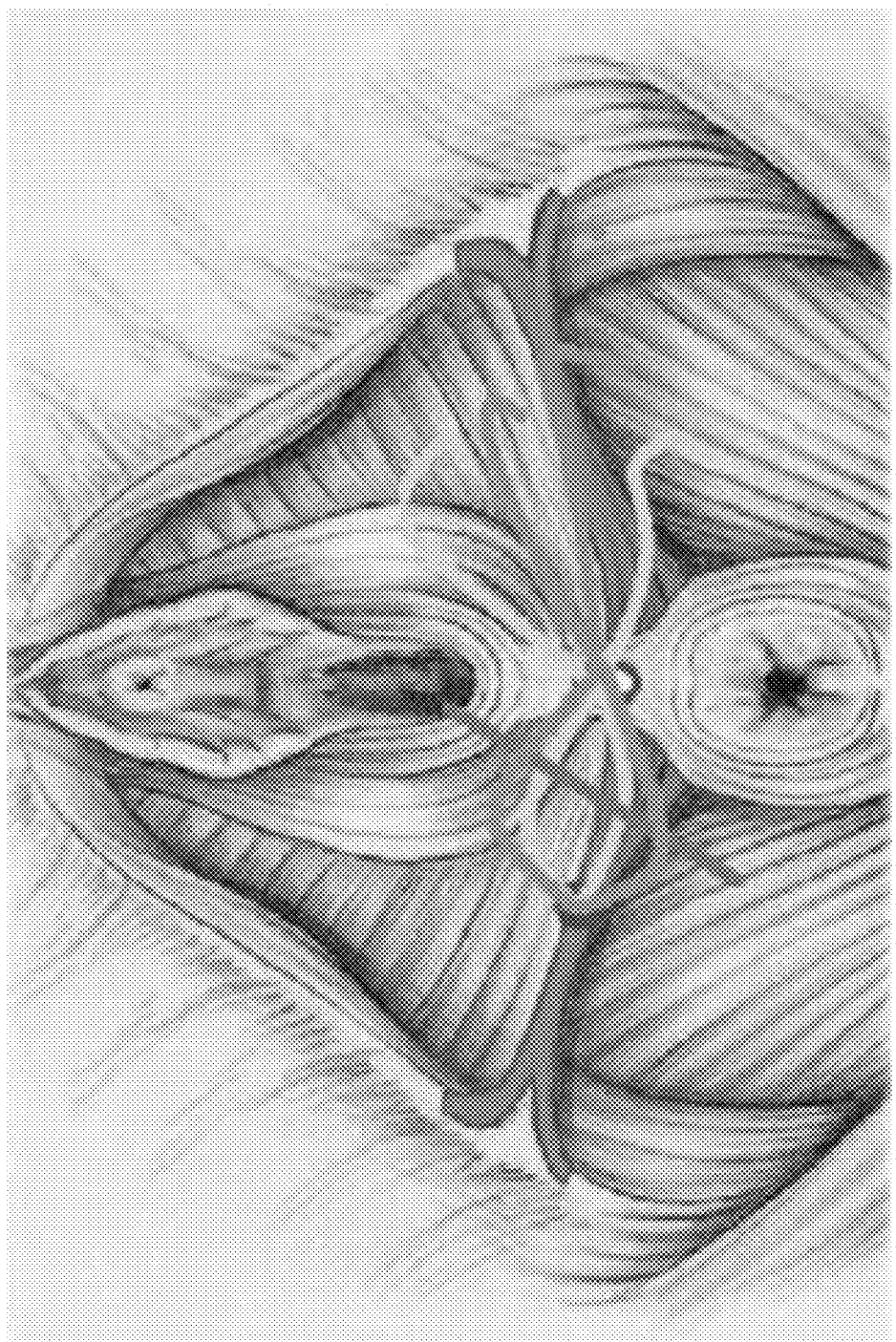
FIG. 6 shows the case in which the right double loop technique is used.

The second example shown in FIG. 6 concerns a left mini-invasive episiotomy plastic surgery with a double suture. The technique used is that of the right dual loop.

In this case two suture threads are used. The two right and left needles of the first light-colored suture thread, are introduced from cut A or cut C, as an outlet hole where a multiple, forehand, backhand or single simple knot is made. In order to introduce the second gray colored suture, the method is repeated, optionally inverting the start point which will be the same cut A or C.

Figure 7:
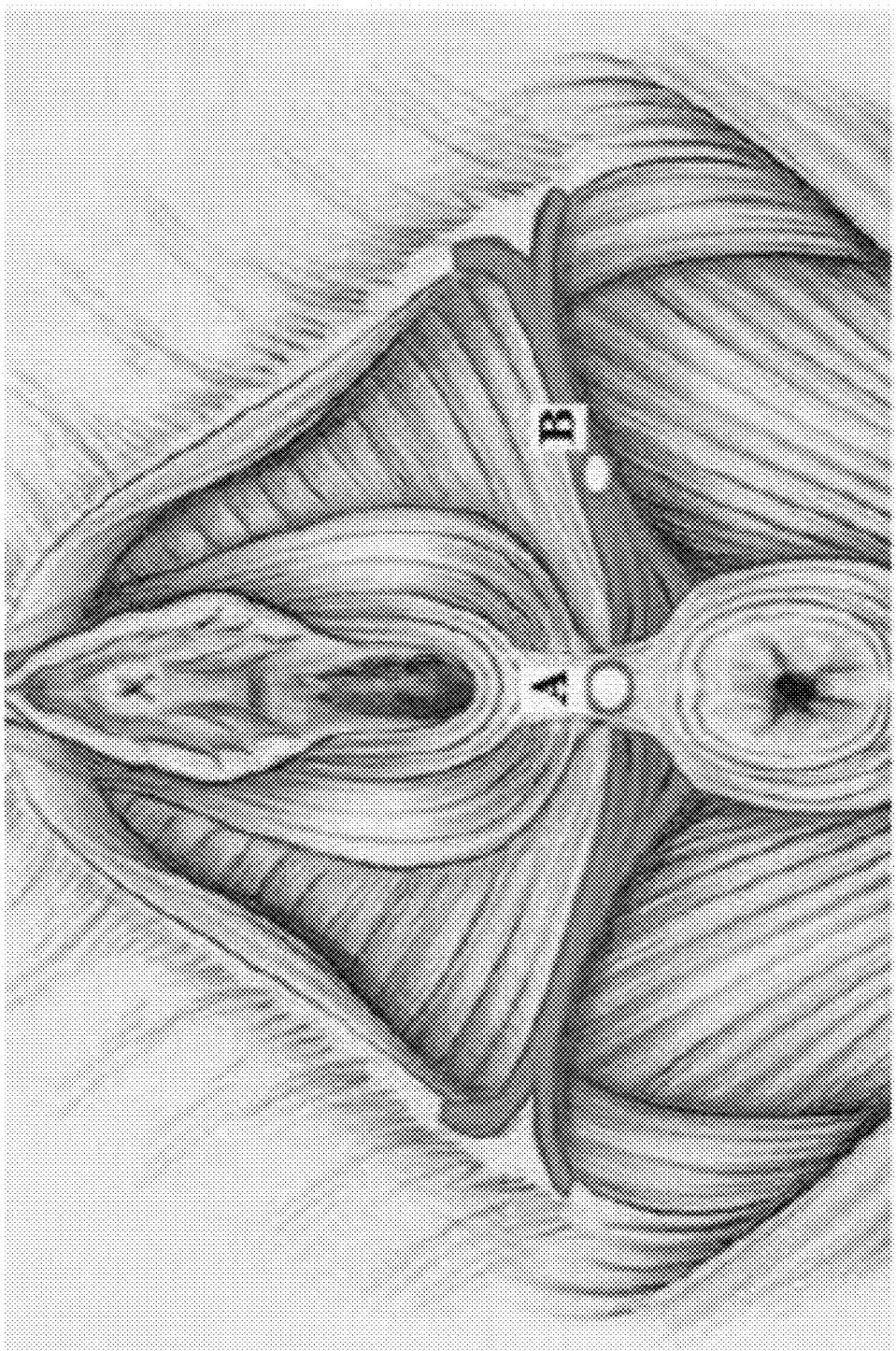
FIG. 7 is an anatomical view of the working plane where the insertion cuts for the left loop technique are highlighted.
Figure 8:
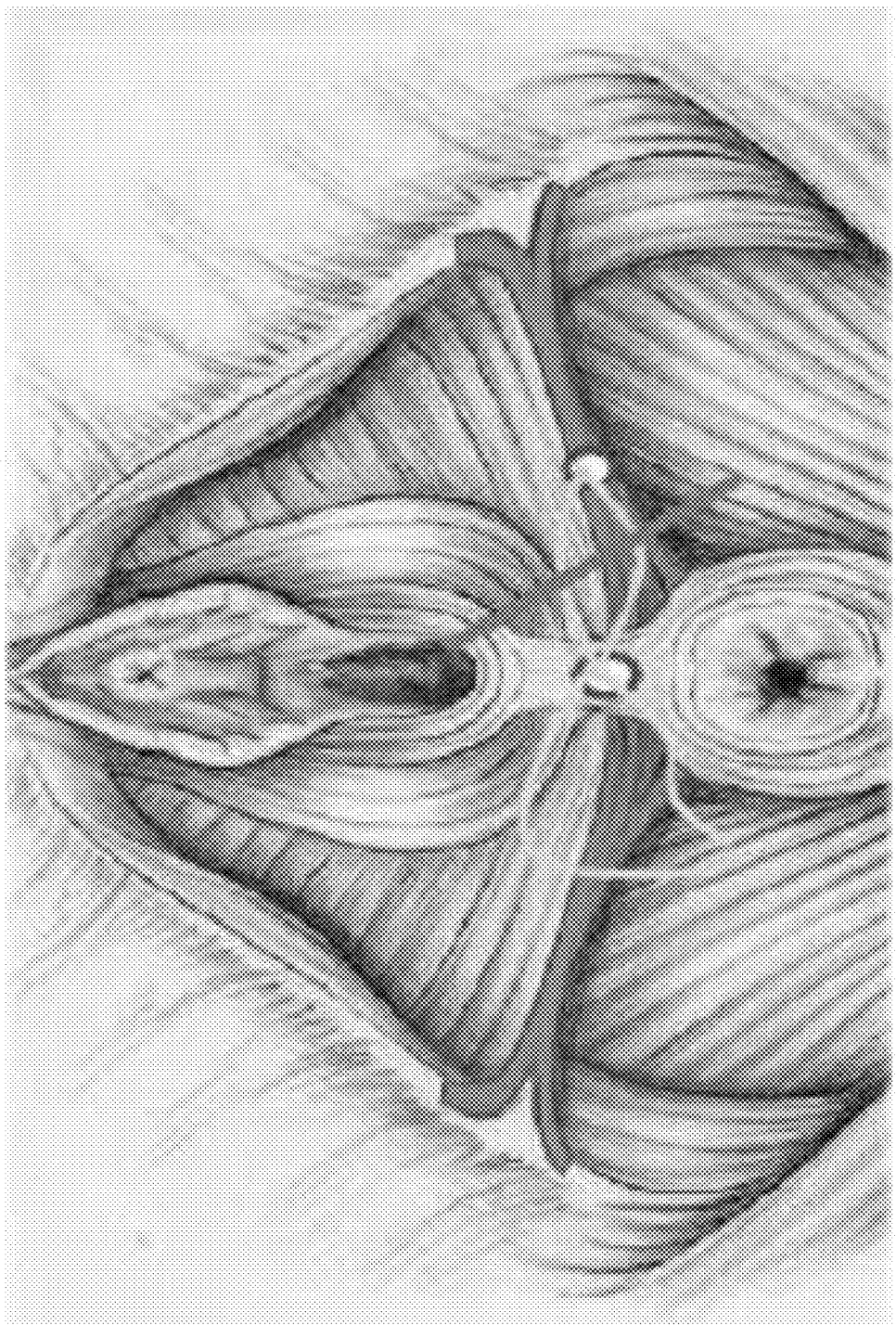
FIG. 8 shows the insertion paths of the thread used with the left single loop technique.
Figure 9:
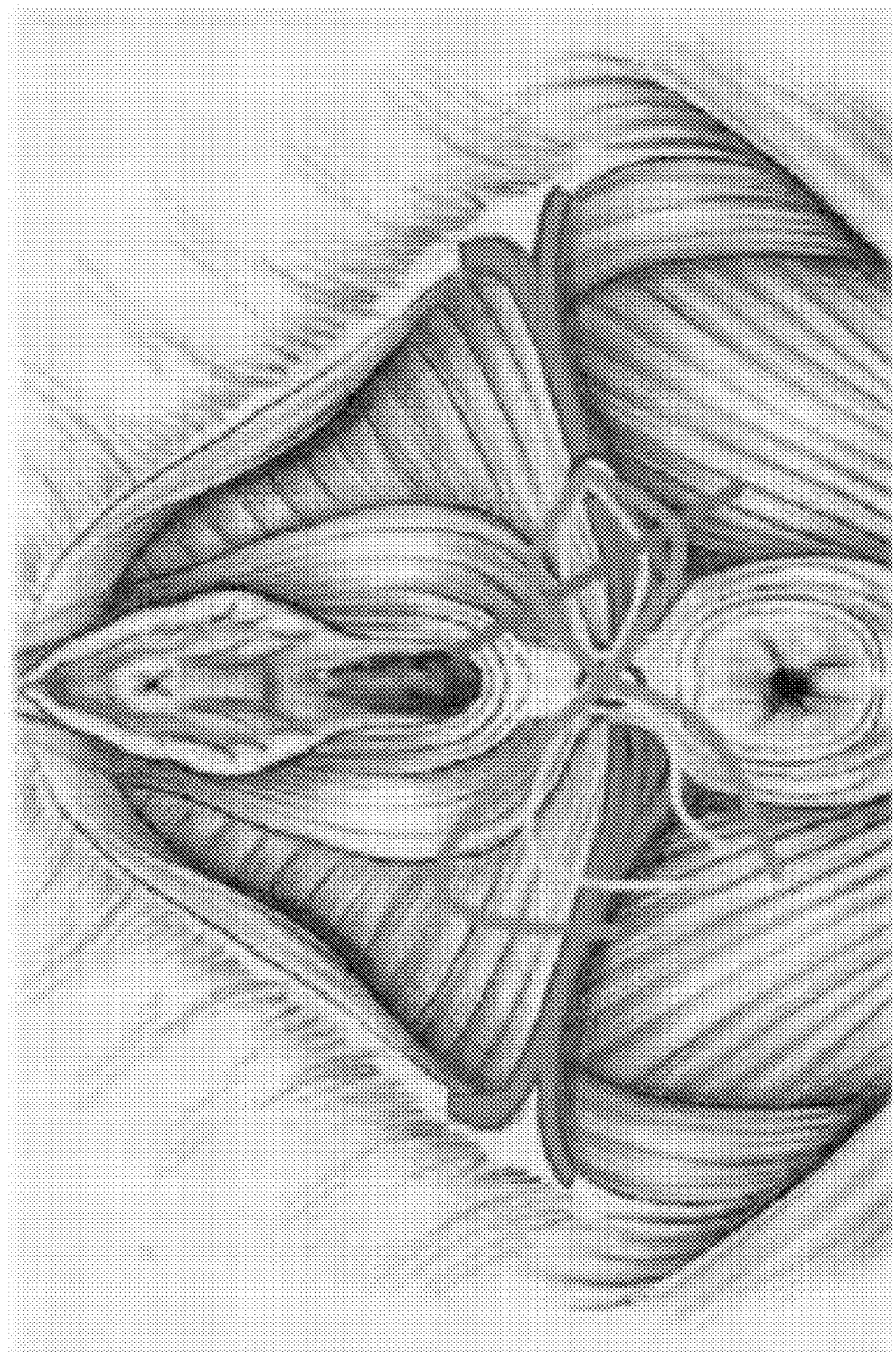
FIG. 9 shows the paths of two threads used when the left double loop technique is used.
Figure 10:
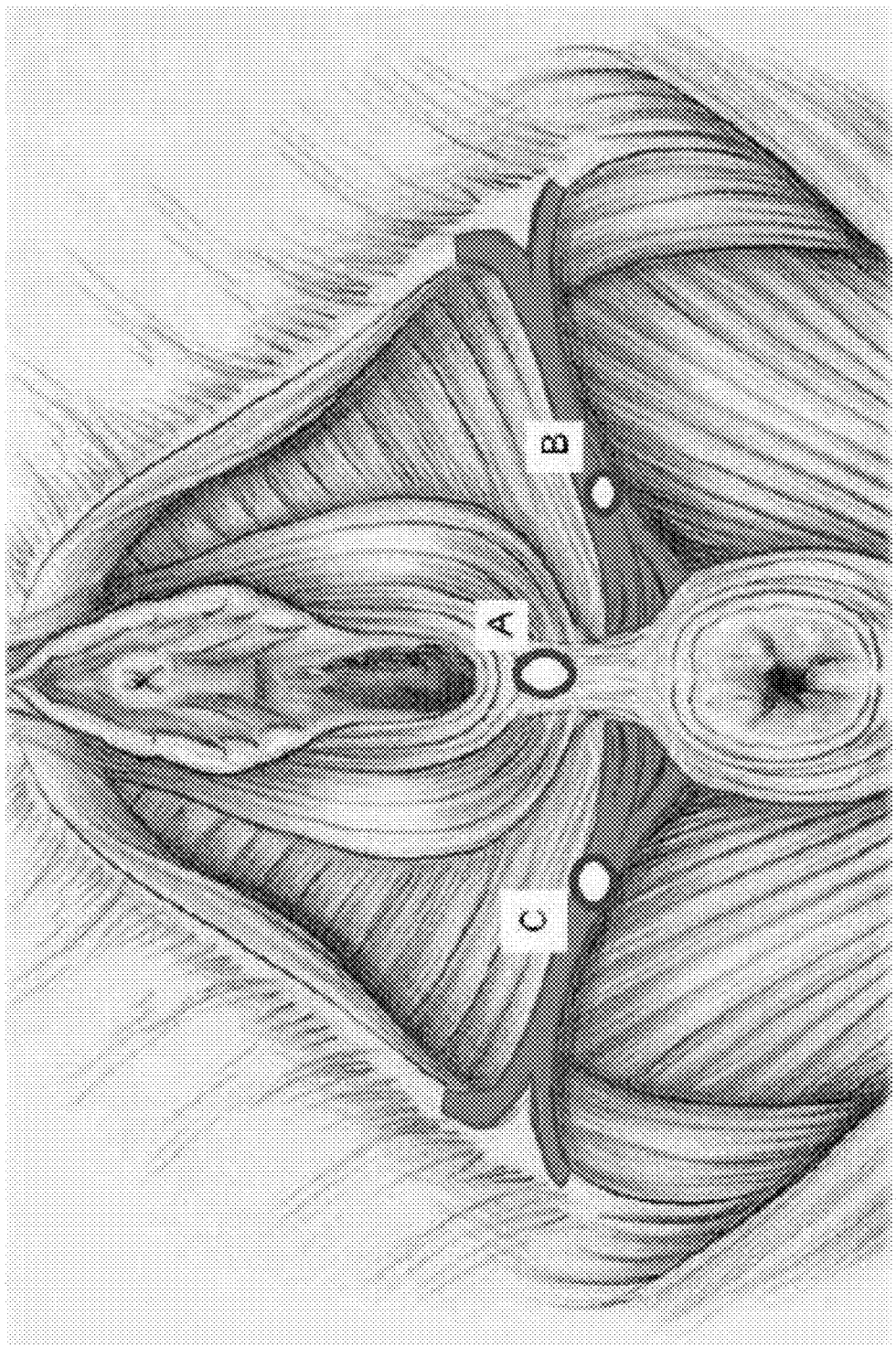
FIG. 10 is an anatomical view of the working plane where the insertion cuts for the triangular loop technique with cranial knot are highlighted.

FIGS. 7, 8 and 9 show the cases of techniques with single and double left loop that differ from the examples in FIGS. 5 and 6 only for the location of the second cut, which is positioned on the left superficial transverse muscle of the female perineum.

FIGS. 10 to 17 show examples of the technique with single or double triangular loop with a knotted cut or caudal knot.

Figure 20:
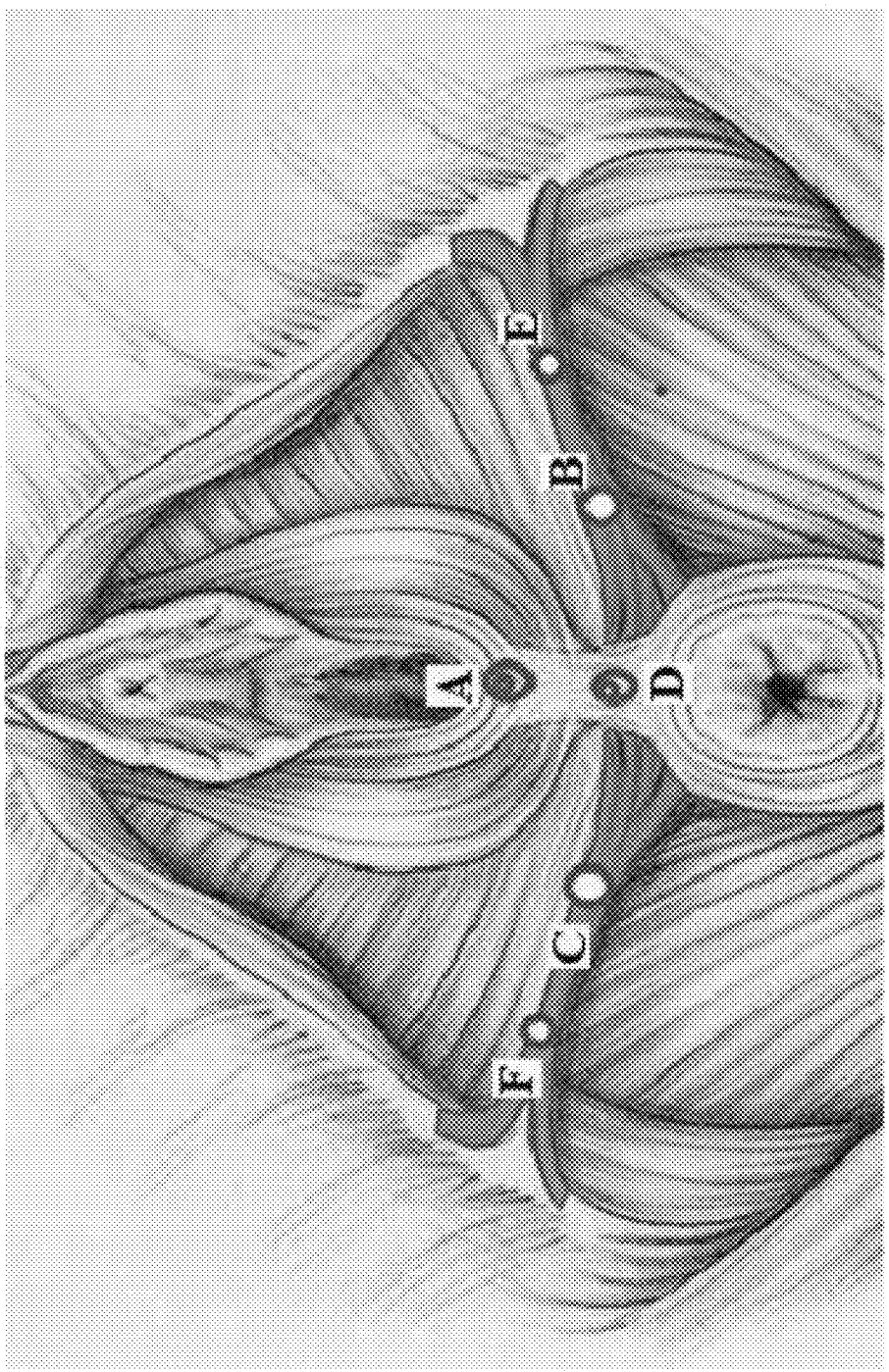
FIG. 20 is an anatomical view of the working plane where the insertion cuts for the quadrangular double loop technique with knotted cranial and/or caudal cut are highlighted.
Figure 21:
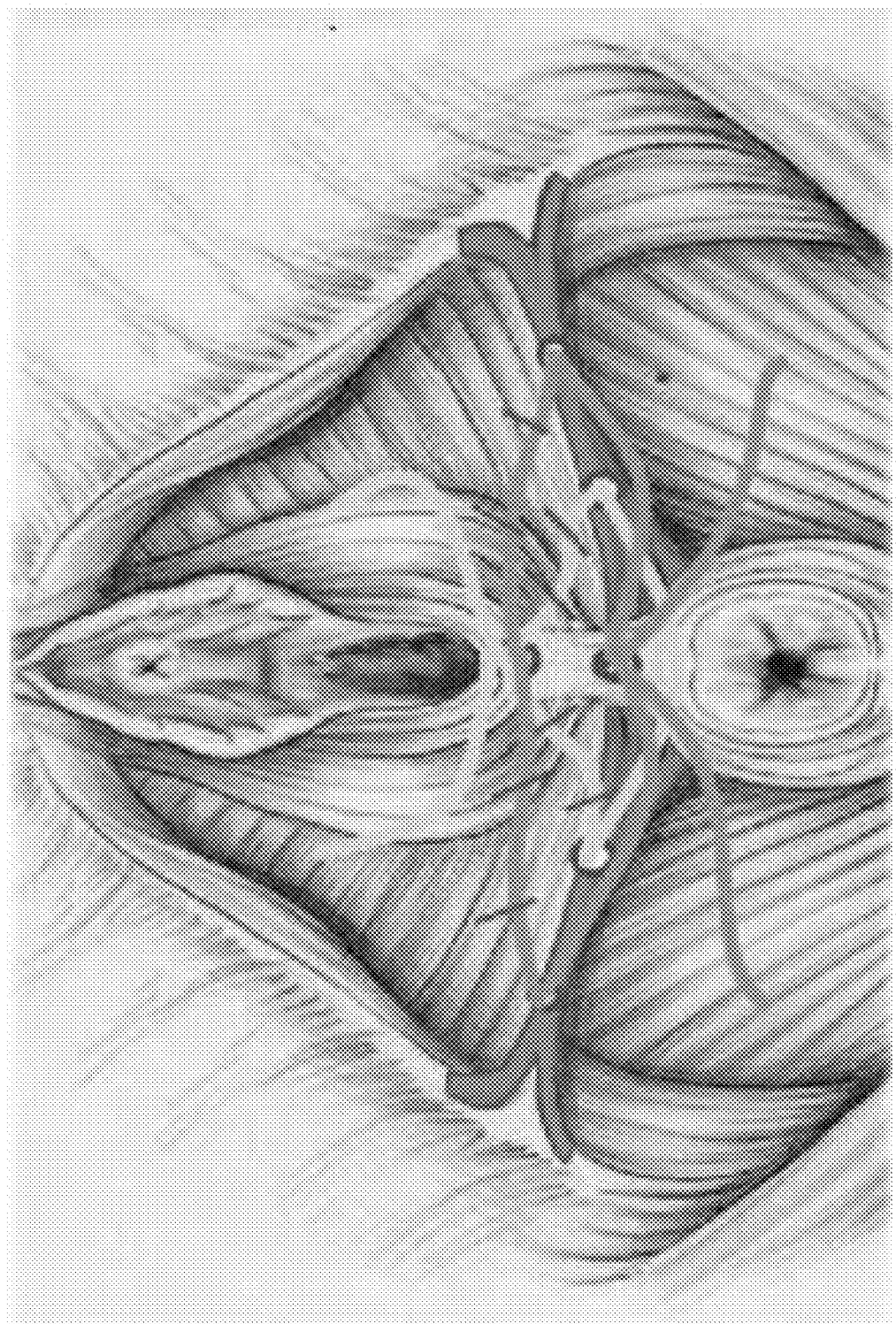
FIG. 21 shows the paths of threads used with the quadrangular or diamond double loop technique with caudal and cranial knot.
Figure 22:
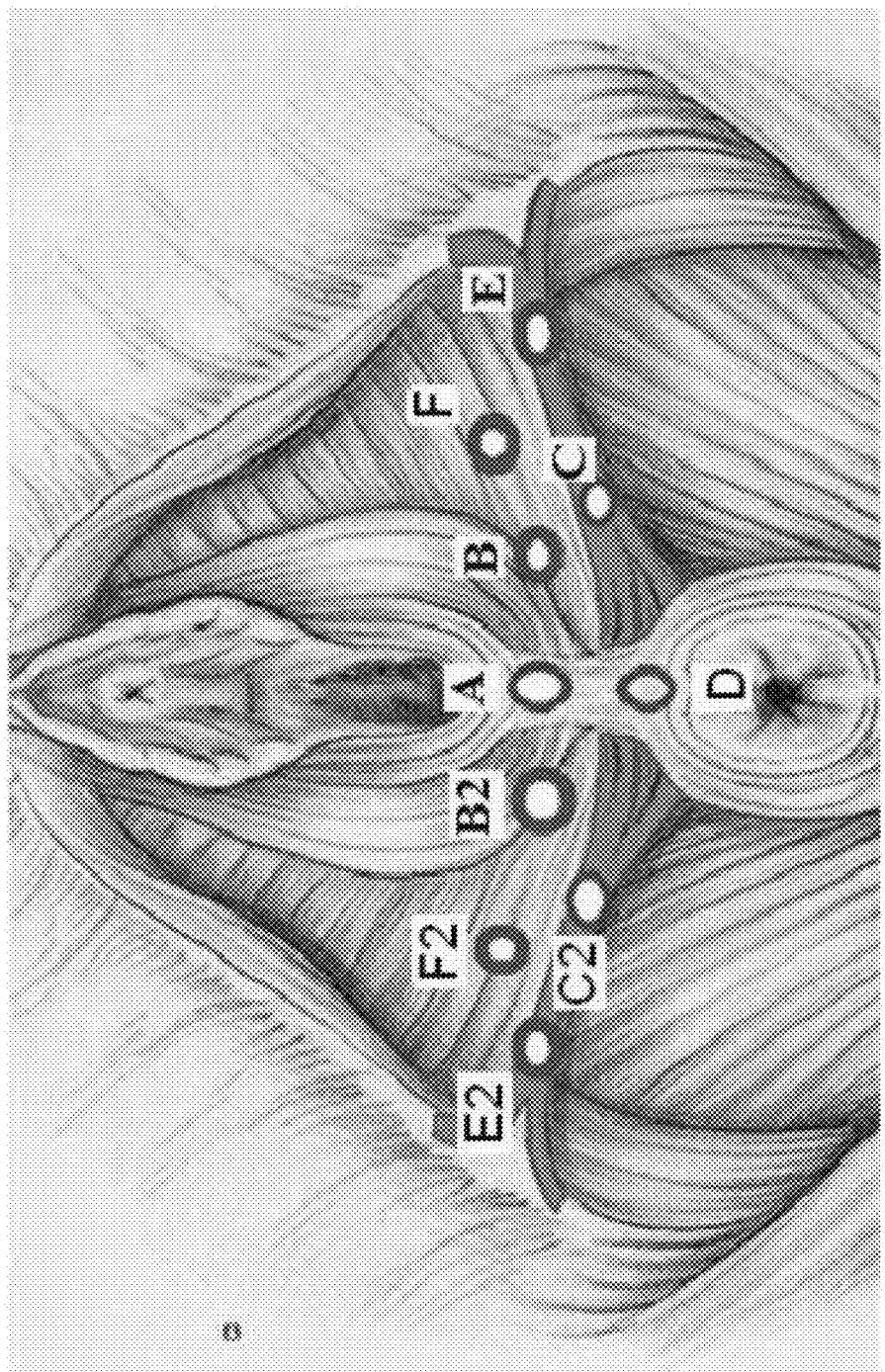
FIG. 22 is an anatomical view of the working plane where the insertion cuts for the polyhedron loop technique on different anatomical planes, with knotted cranial and/or caudal cut, are highlighted.
Figure 23:
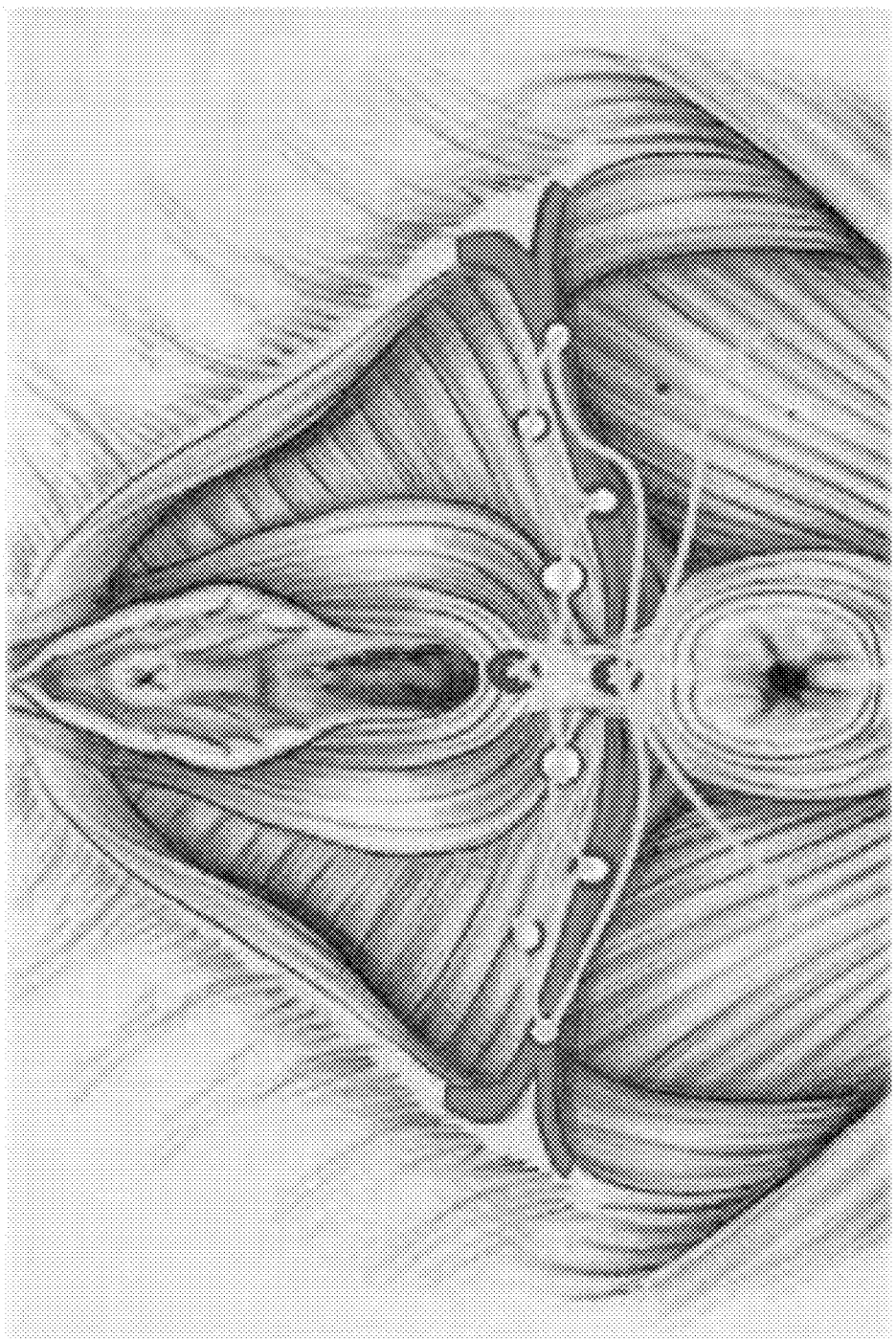
FIG. 23 shows the insertion paths for the polyhedron loop technique o different anatomical planes, with knotted cranial and/or caudal cut.
Figure 24:
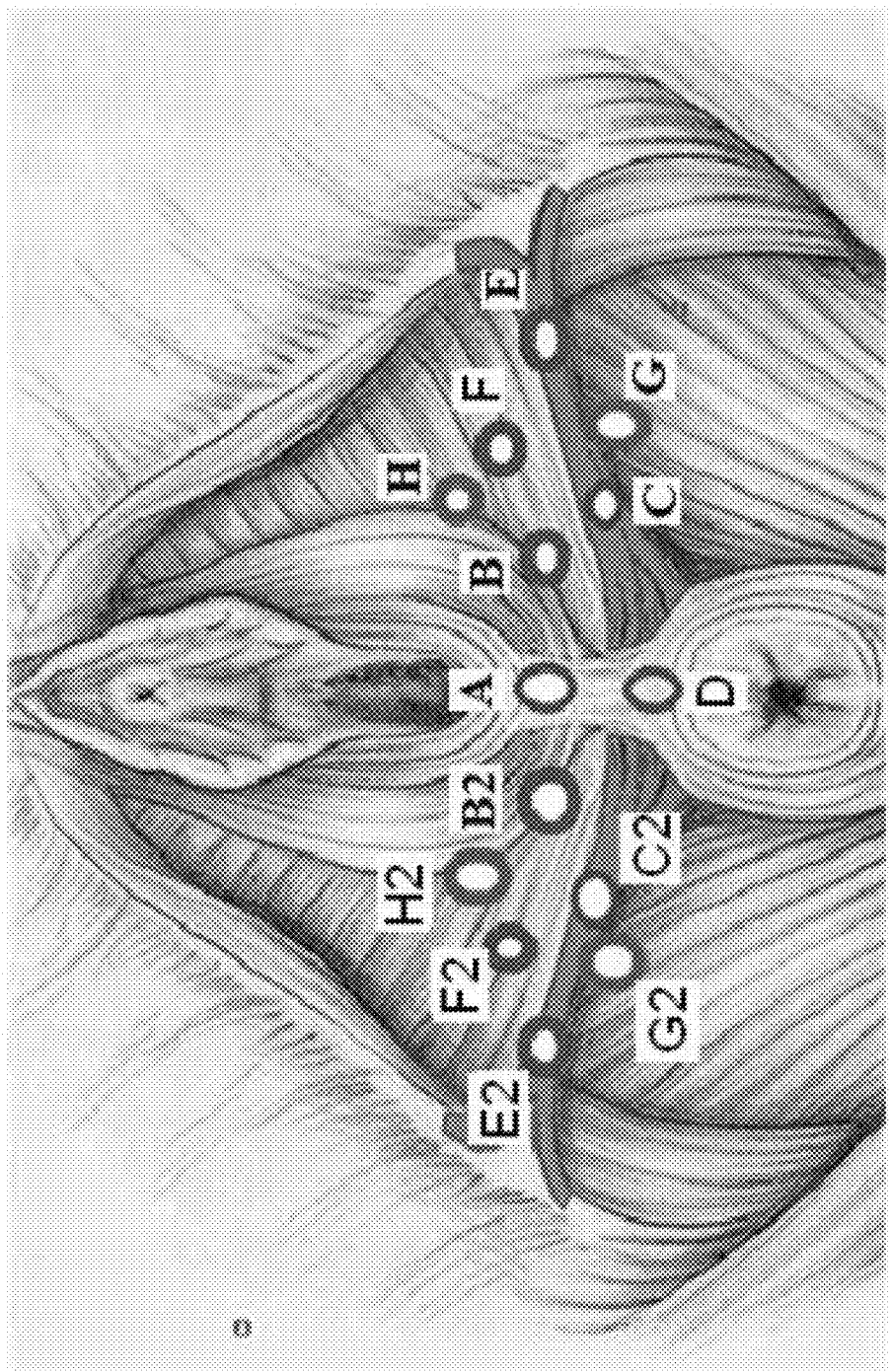
FIG. 24 is an anatomical view of the working plane where the insertion cuts for the polyhedron double and/or triple and/or quadruple loop technique on different anatomical planes, with knotted cranial and/or caudal cut, are highlighted.
Figure 25:
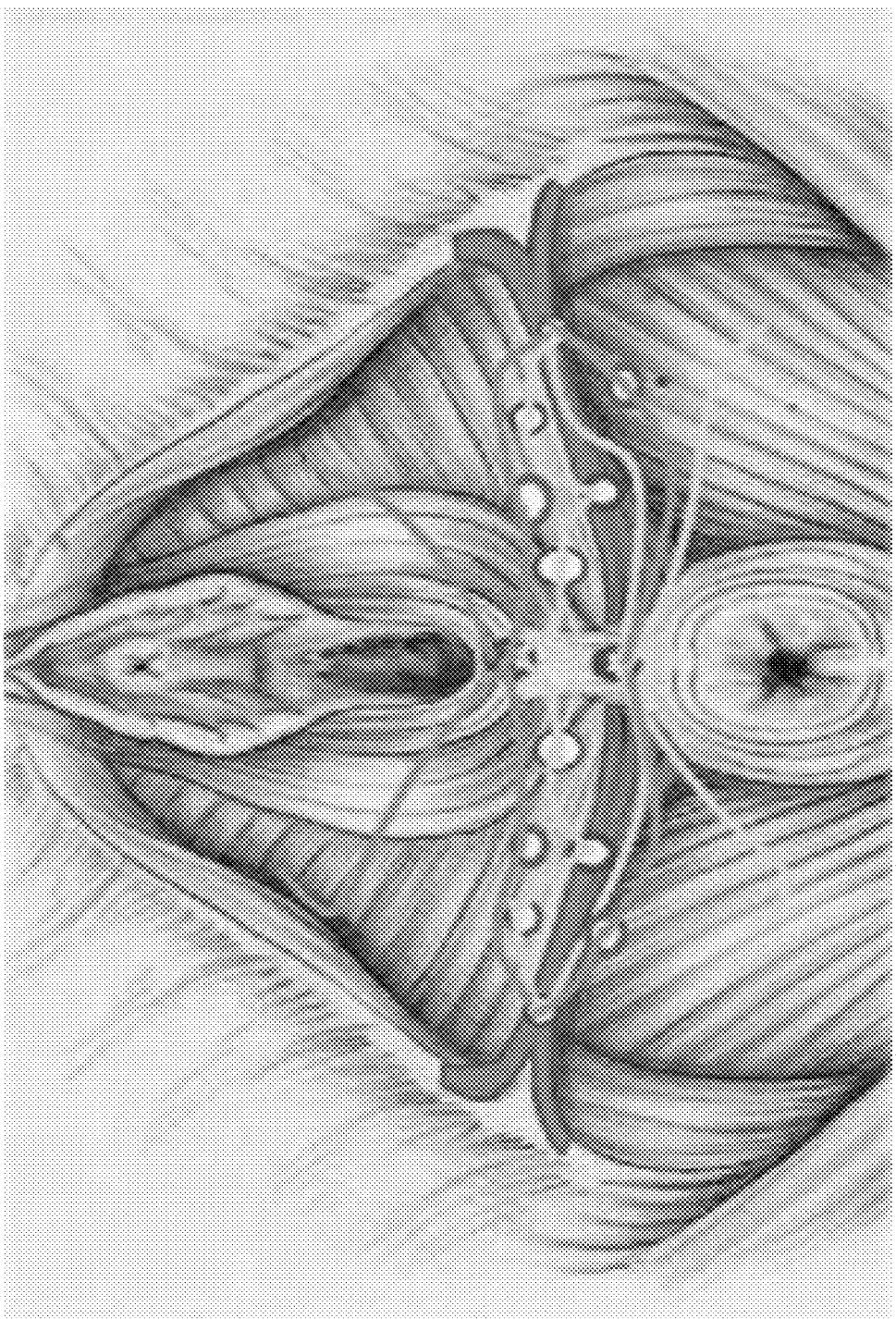
FIG. 25 shows the path of the threads used for the polyhedron double and/or triple and/or quadruple loop technique on different anatomical planes, with knotted cranial and/or caudal cut.
Figure 26:
FIGS. 26 to 45 show in sequence the steps of the technique used according to preferred examples of the invention, in particular.

More complex surgeries are shown in FIGS. 20-22.

FIG. 20 shows the sequence for inserting two sutures with a double quadrangular loop technique with knotted cranial and/or caudal cut.

The first suture can be introduced from cut A or D, indifferently. With the two right and left needles, depending on the case we emerge from cut D or A, where a multiple simple knot is made, which knot can be simple, forehand, backhand, single, obviously after emerging from and returning, respectively, to the cuts located on the right and left oblique axes, B and C, or even C and B, which are only transit cuts. The second suture is then introduced from cut A or D, indifferently. With the two right and left needles, we emerge from cut D or A where a multiple, simple knot is made, which knot can be forehand, backhand, single, obviously after emerging from and returning, respectively, to the cuts located on the right and left oblique axes E and F or even F and E, which are only transit cuts.

FIG. 22 shows the insertion cuts for the polyhedron loop technique on different anatomical planes with knotted and/or caudal cut.

The operative technique in brief is as follows.

Figure 27:
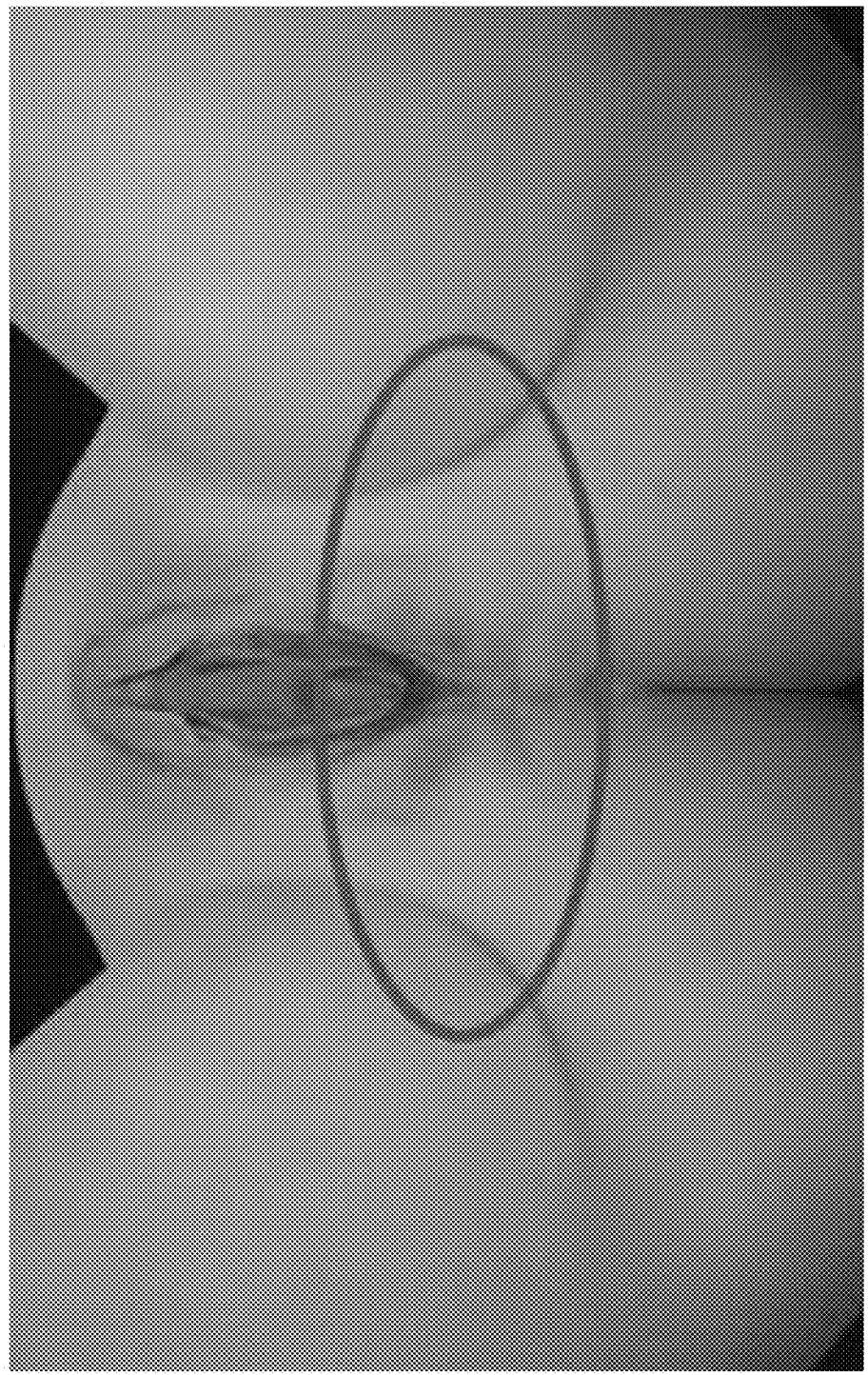
Figure 28:
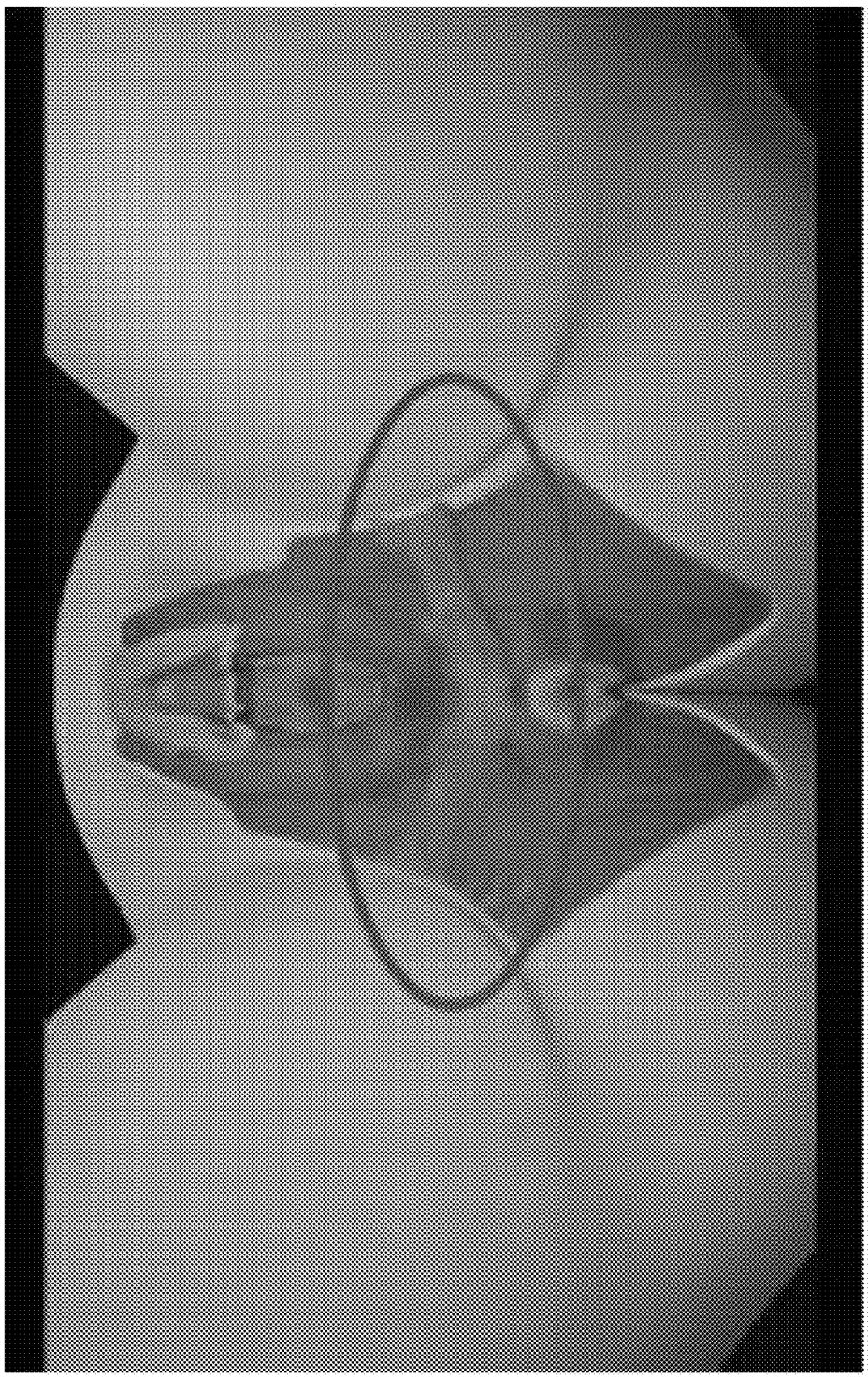
Figure 29:
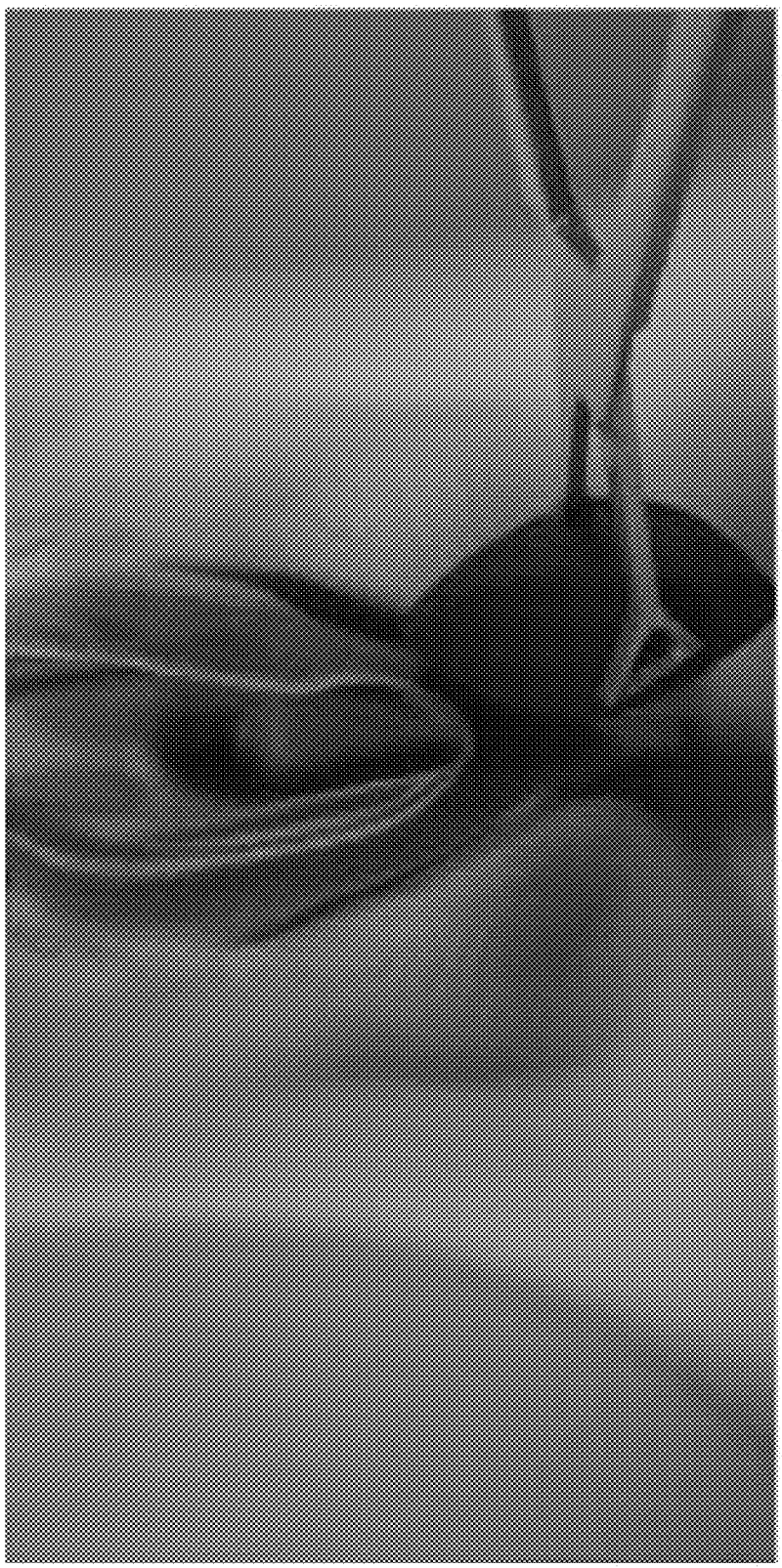
Figure 30:
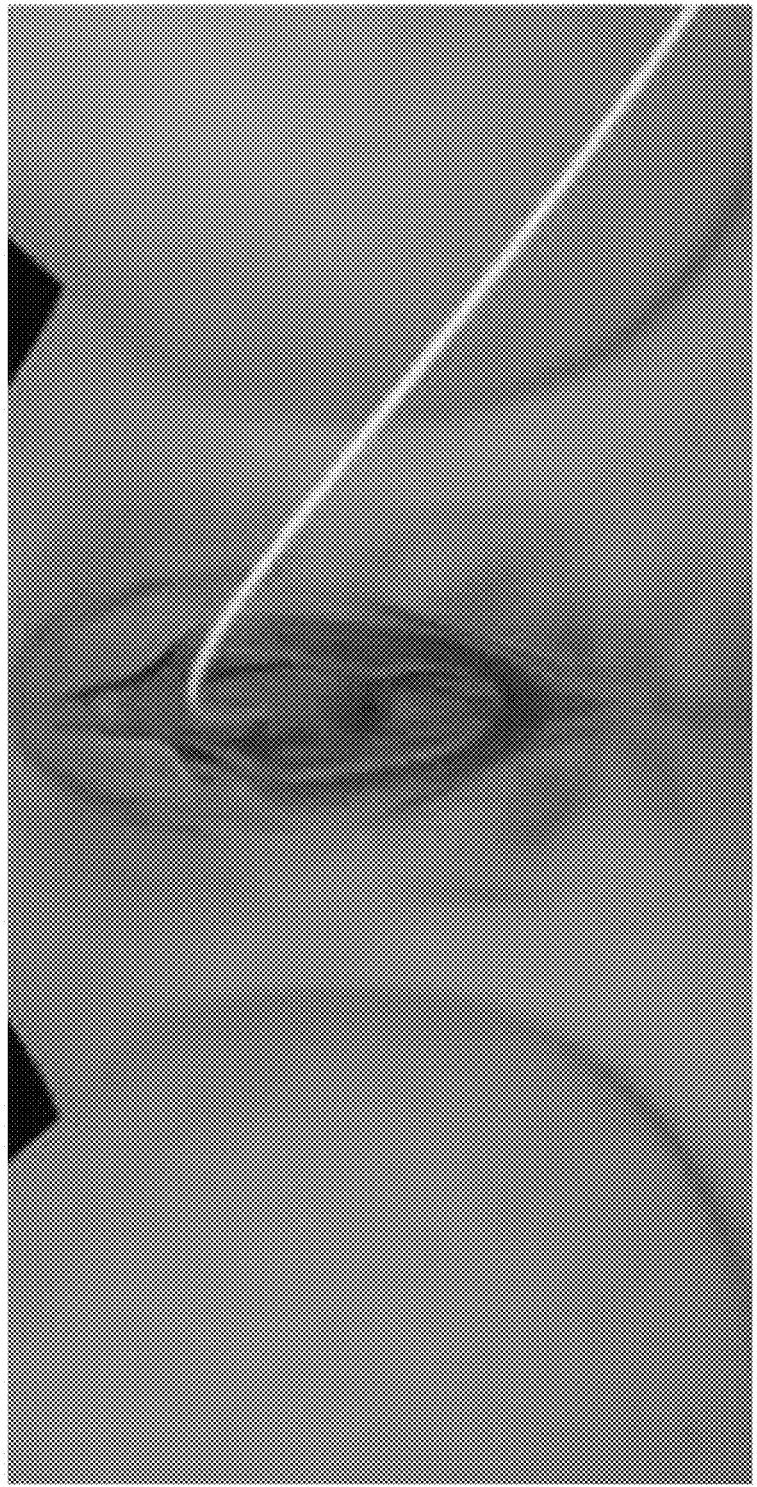
Figure 31:
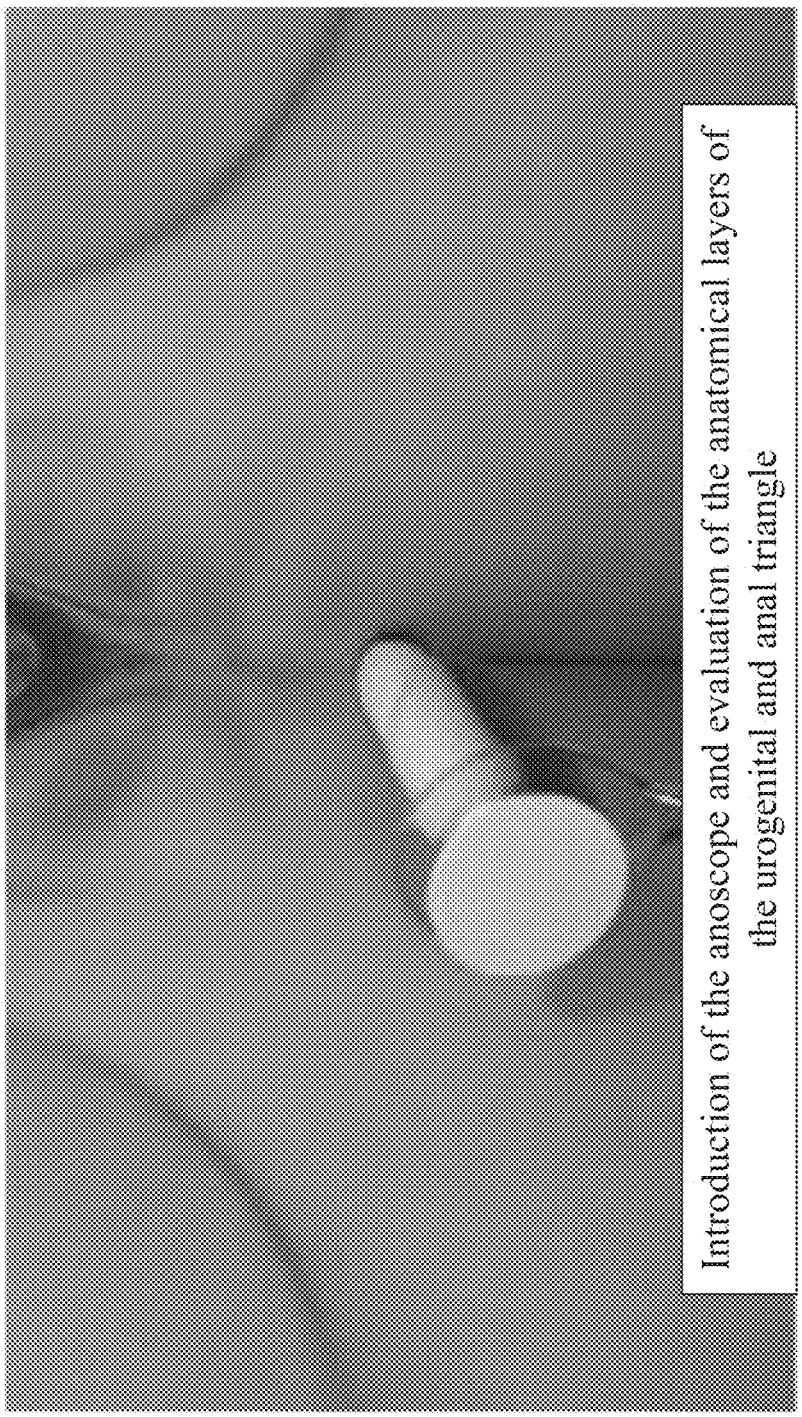
Figure 32:
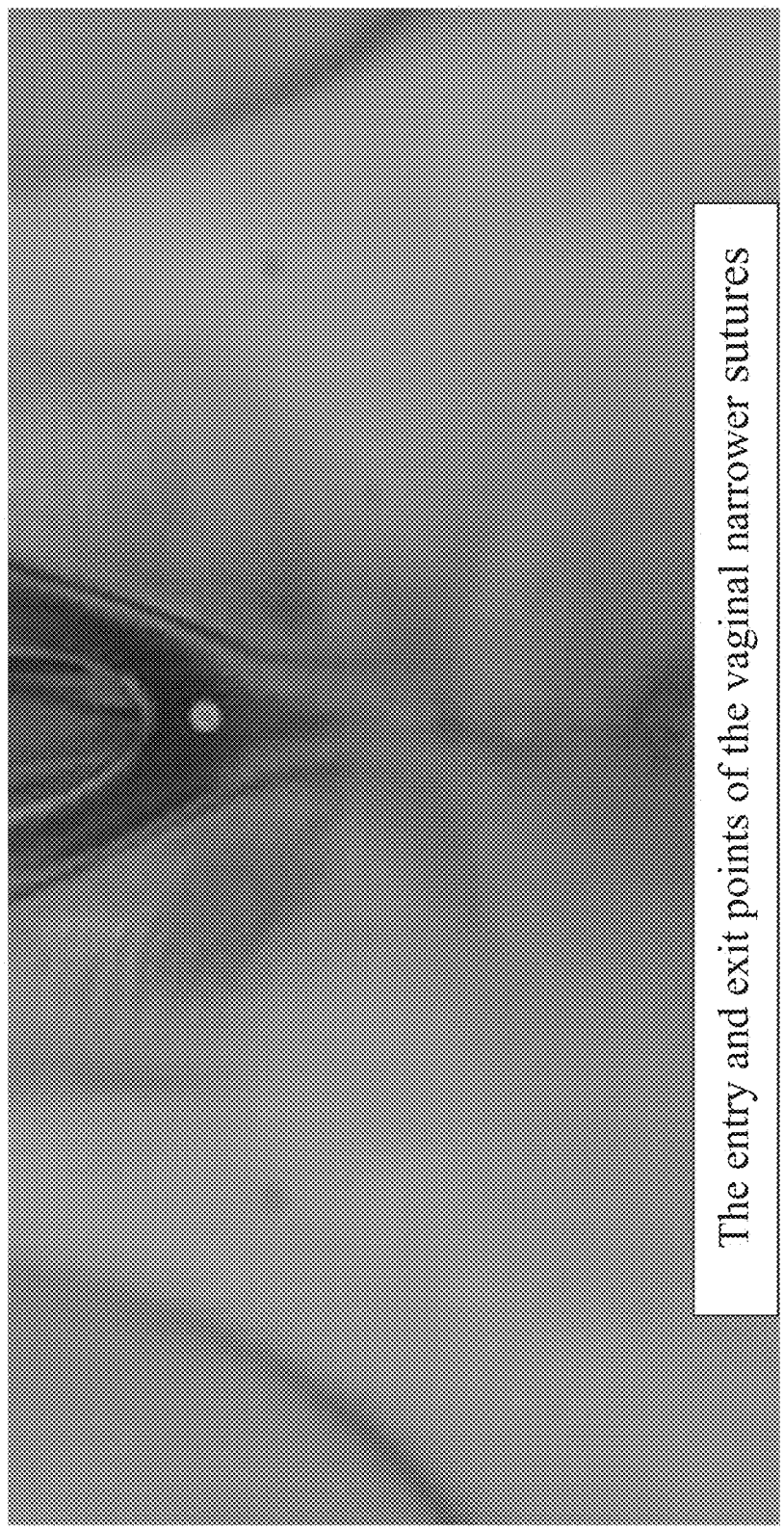
Figure 33:
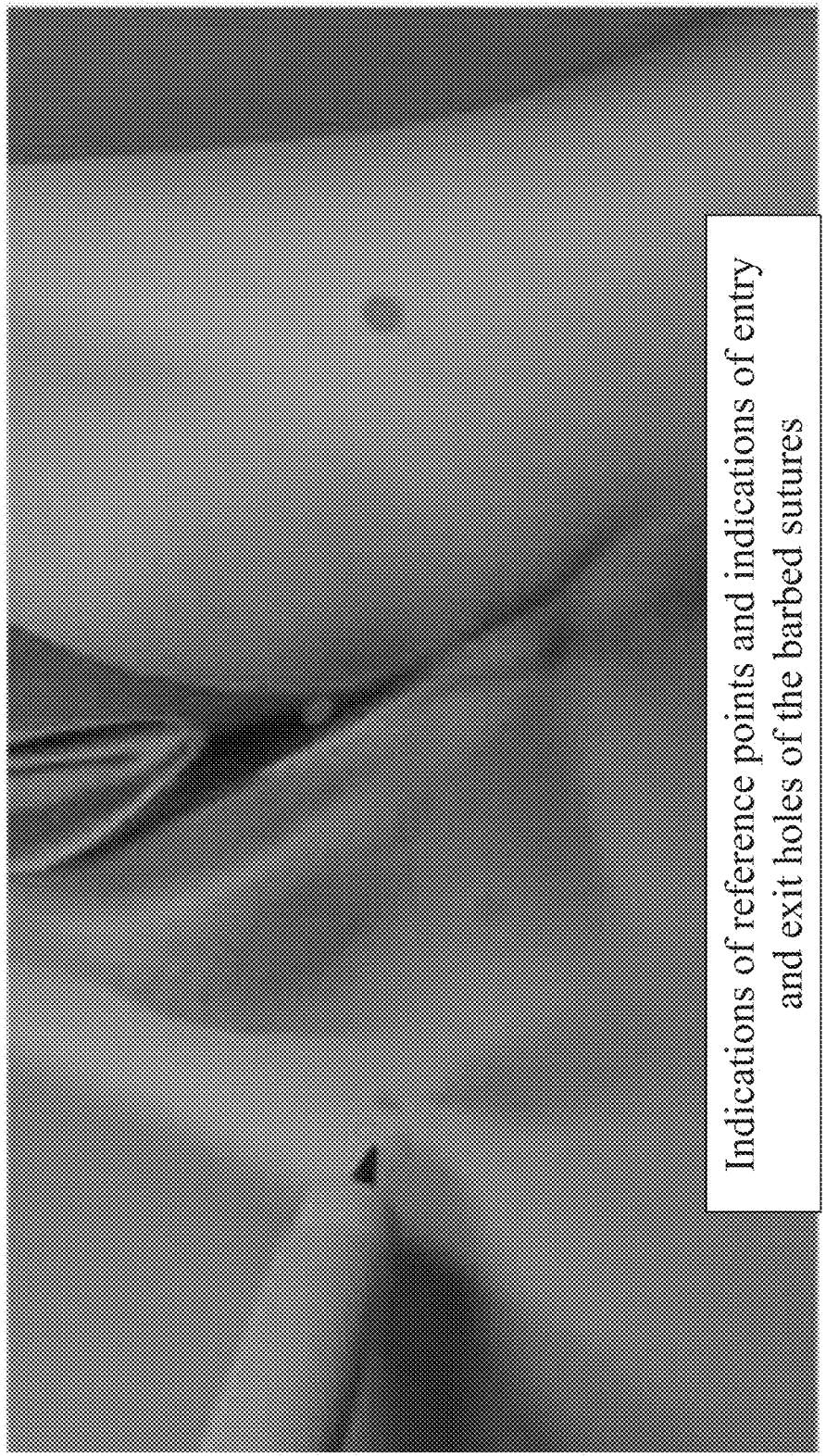
Figure 34:
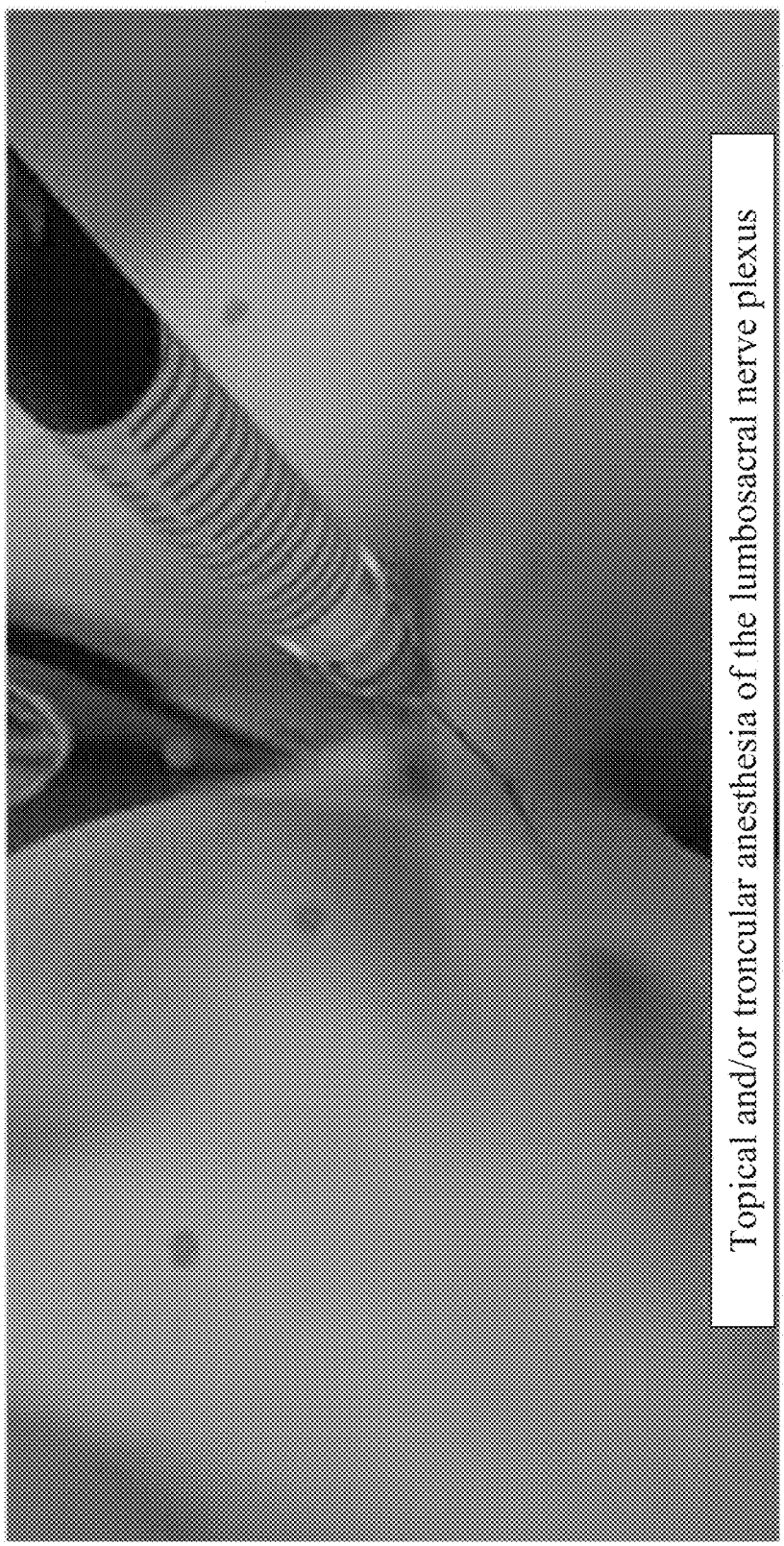
Figure 35:
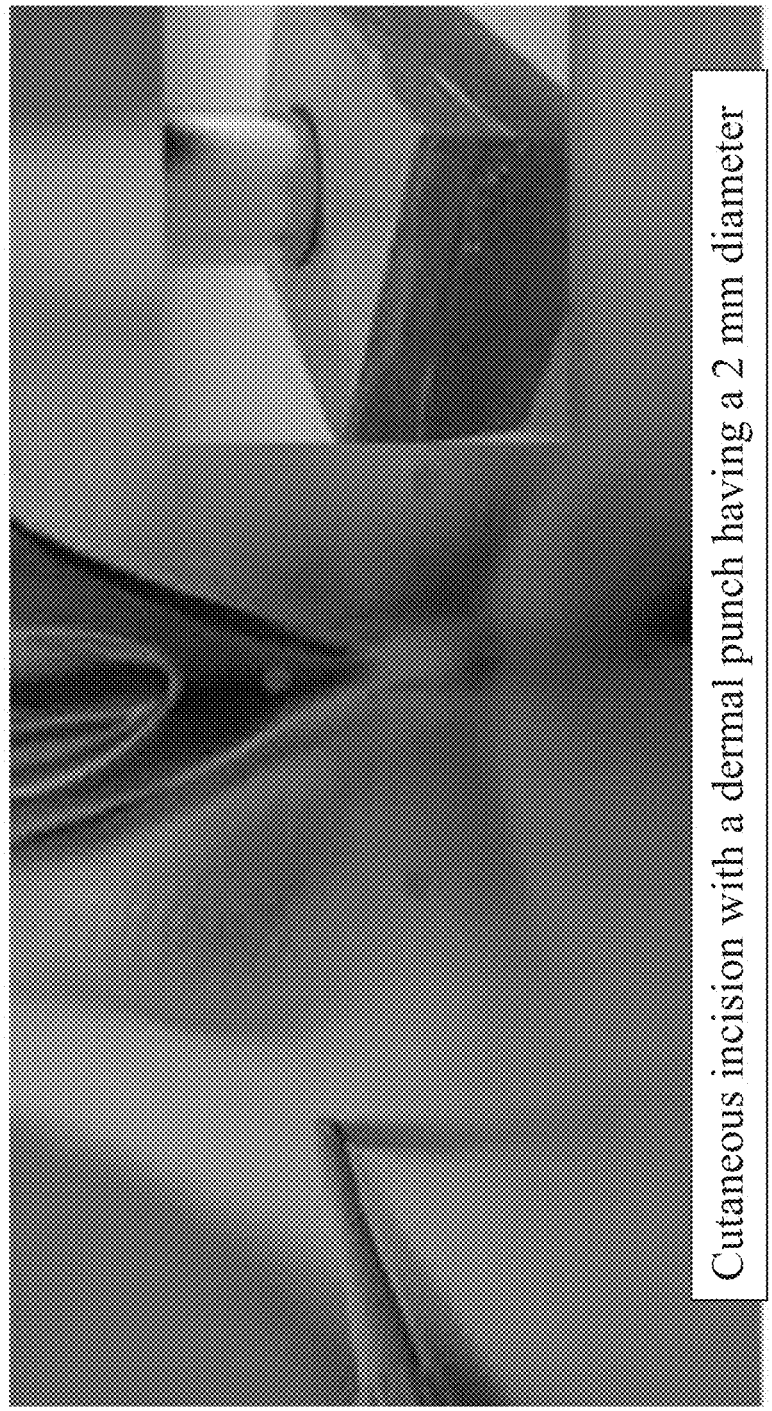
Figure 36:
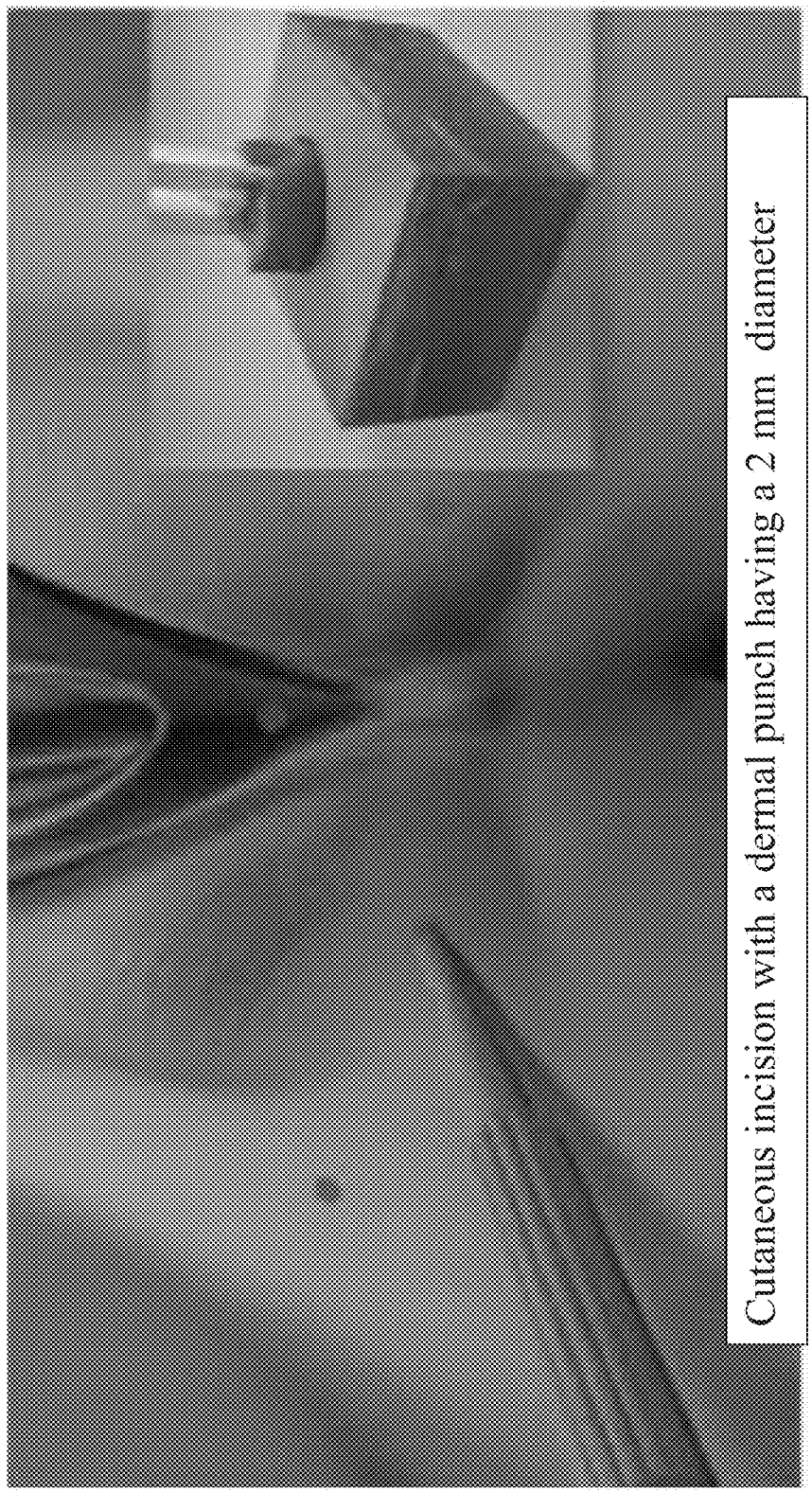
Figure 37:
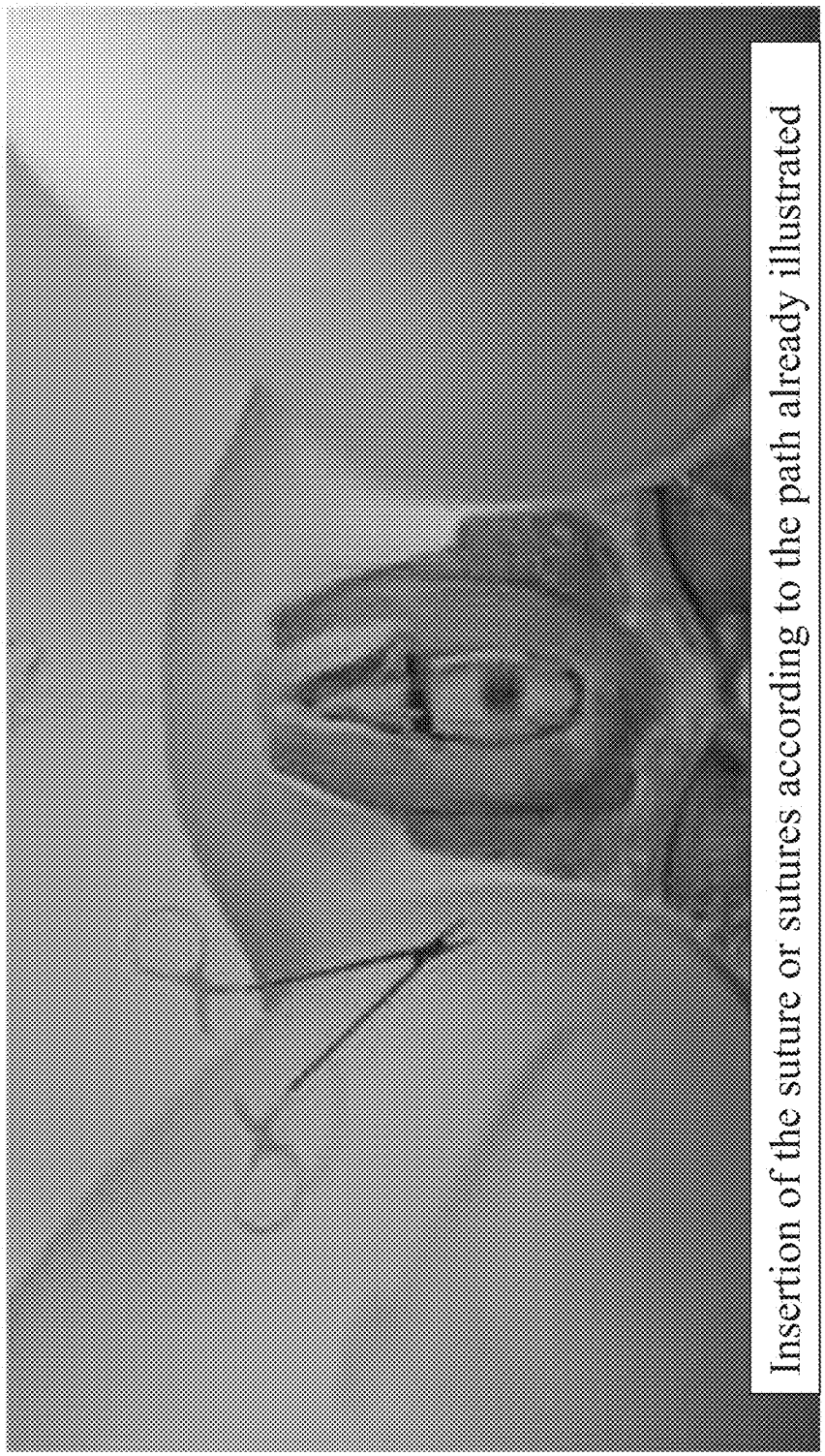
Figure 38:
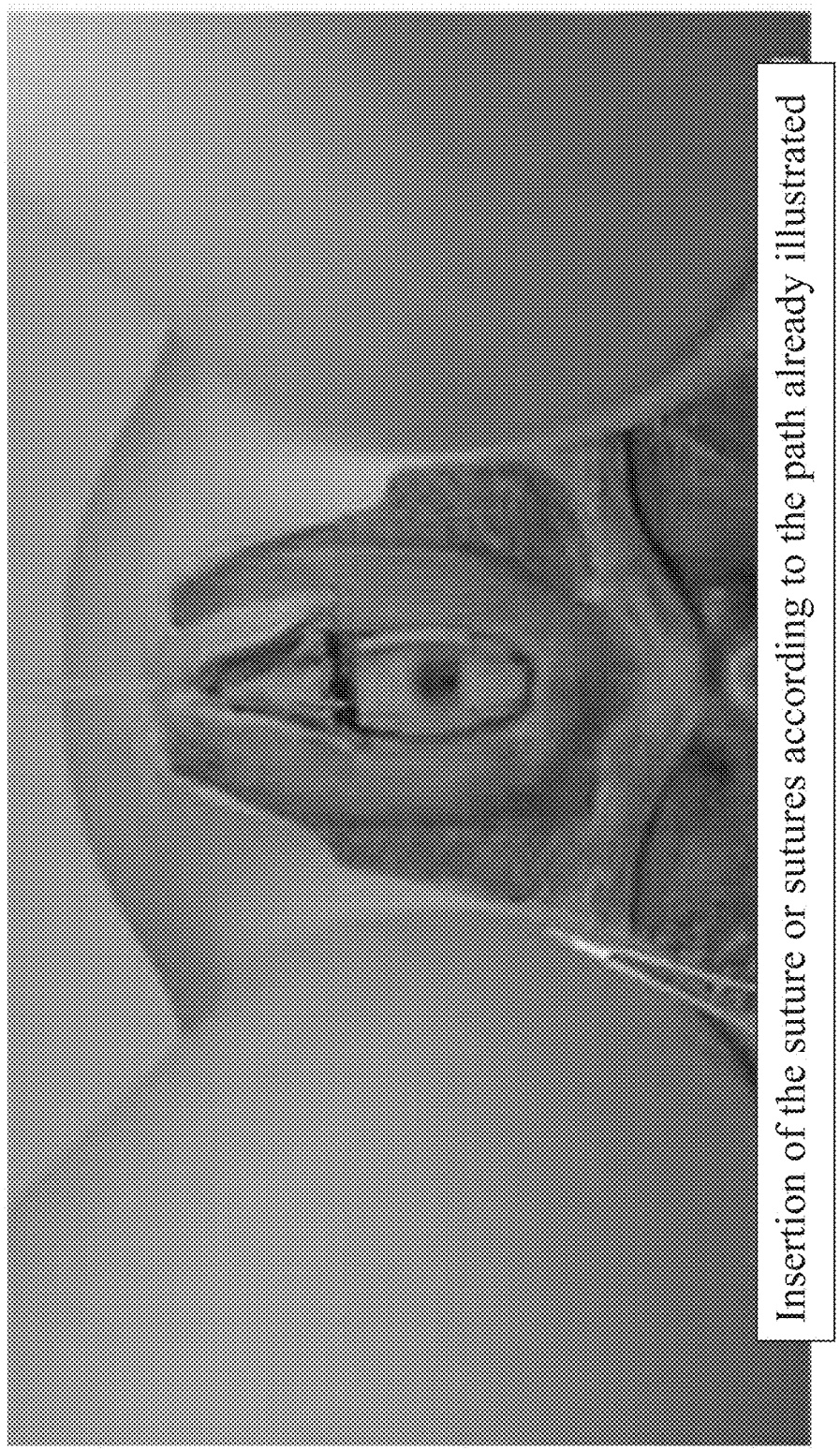
Figure 39:
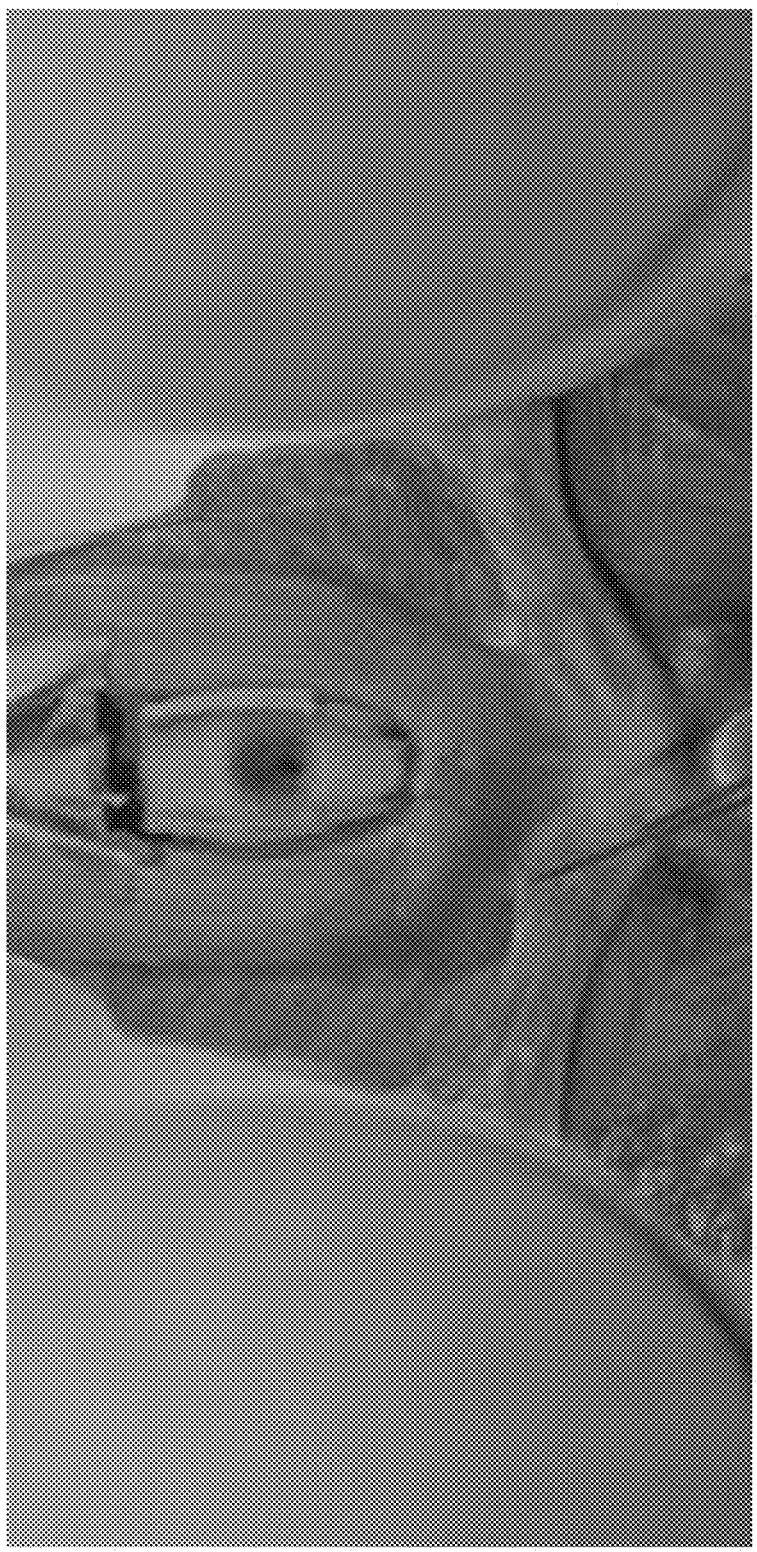
Figure 40:
Figure 41:
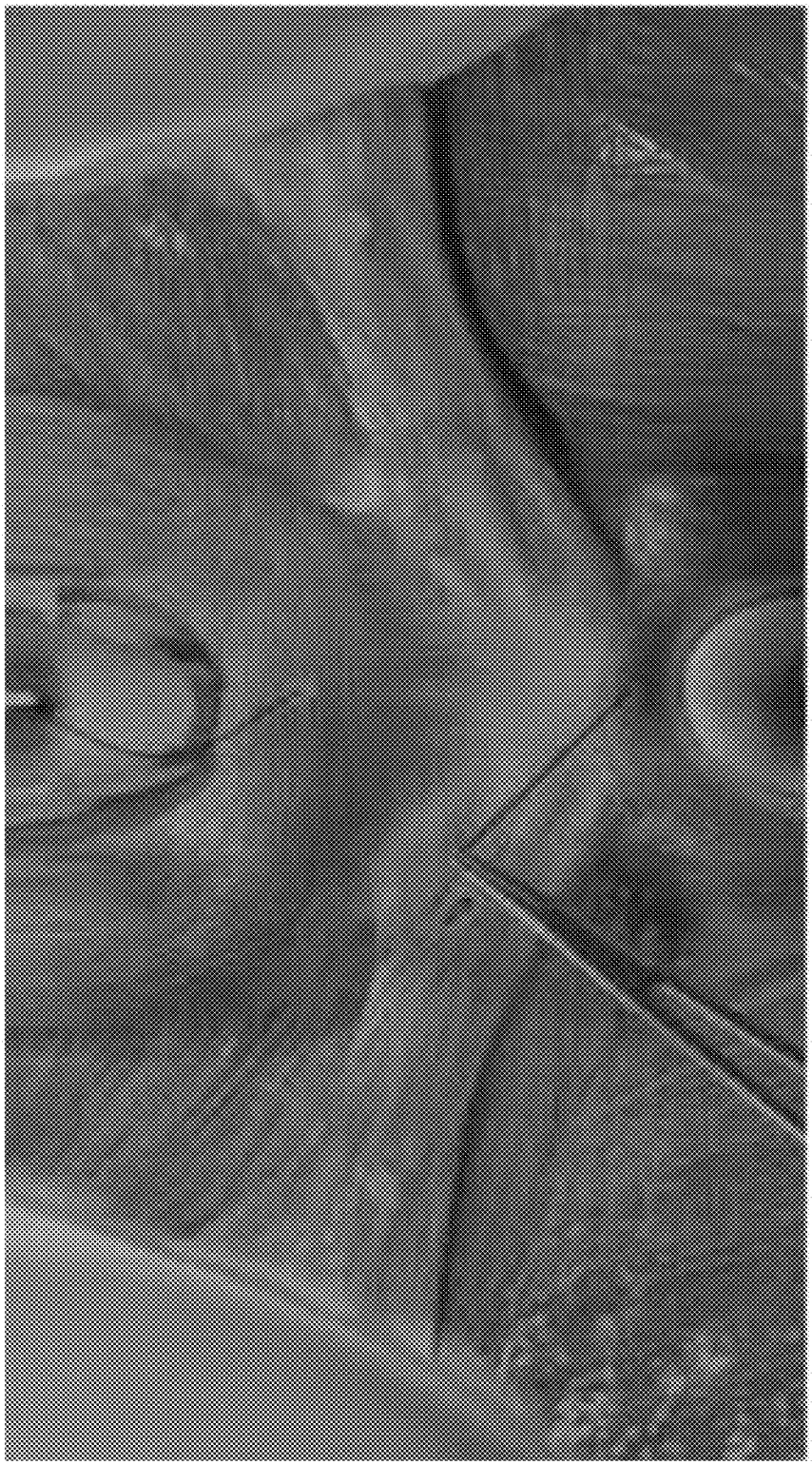
Figure 42:
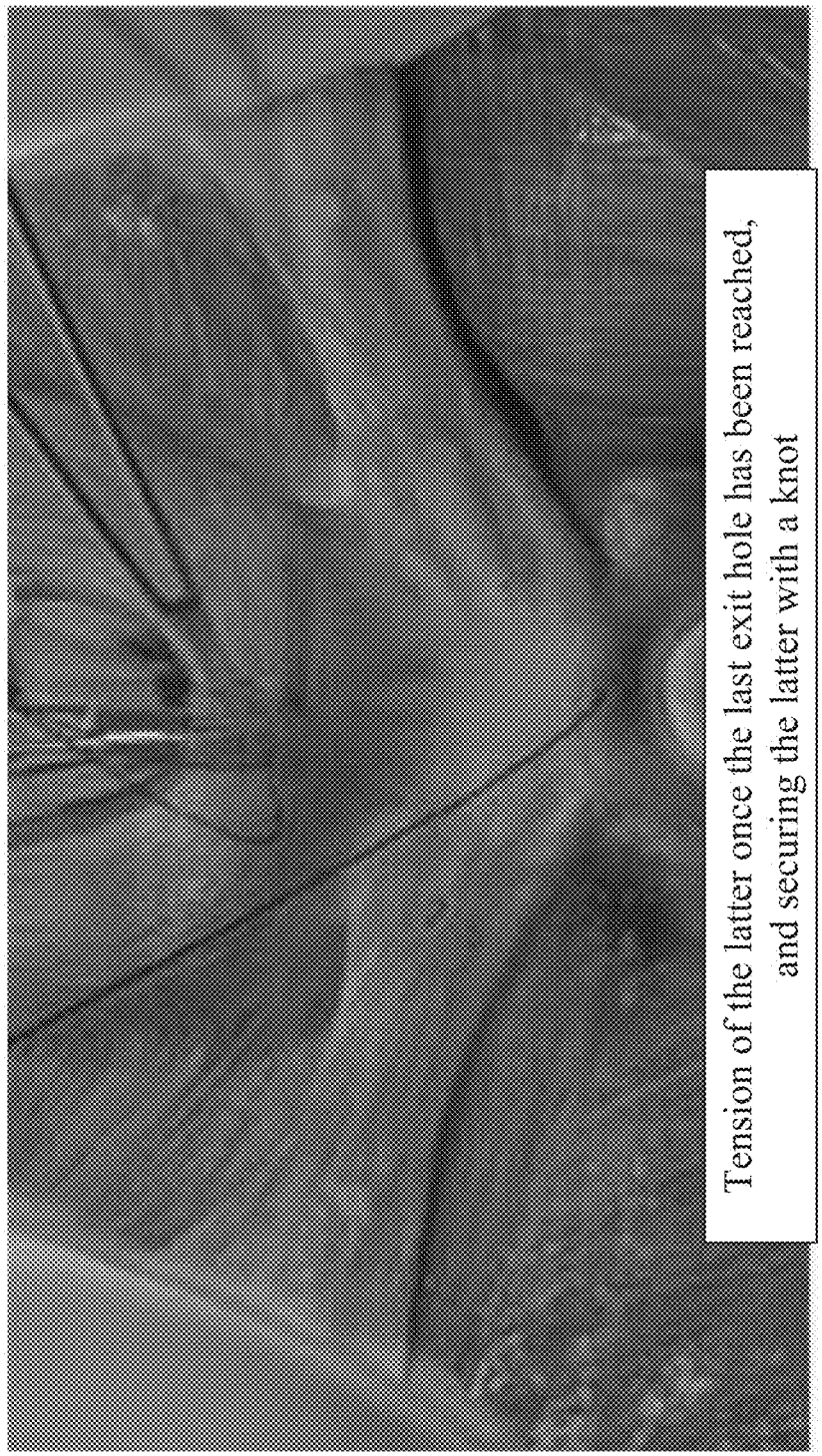
Figure 43:
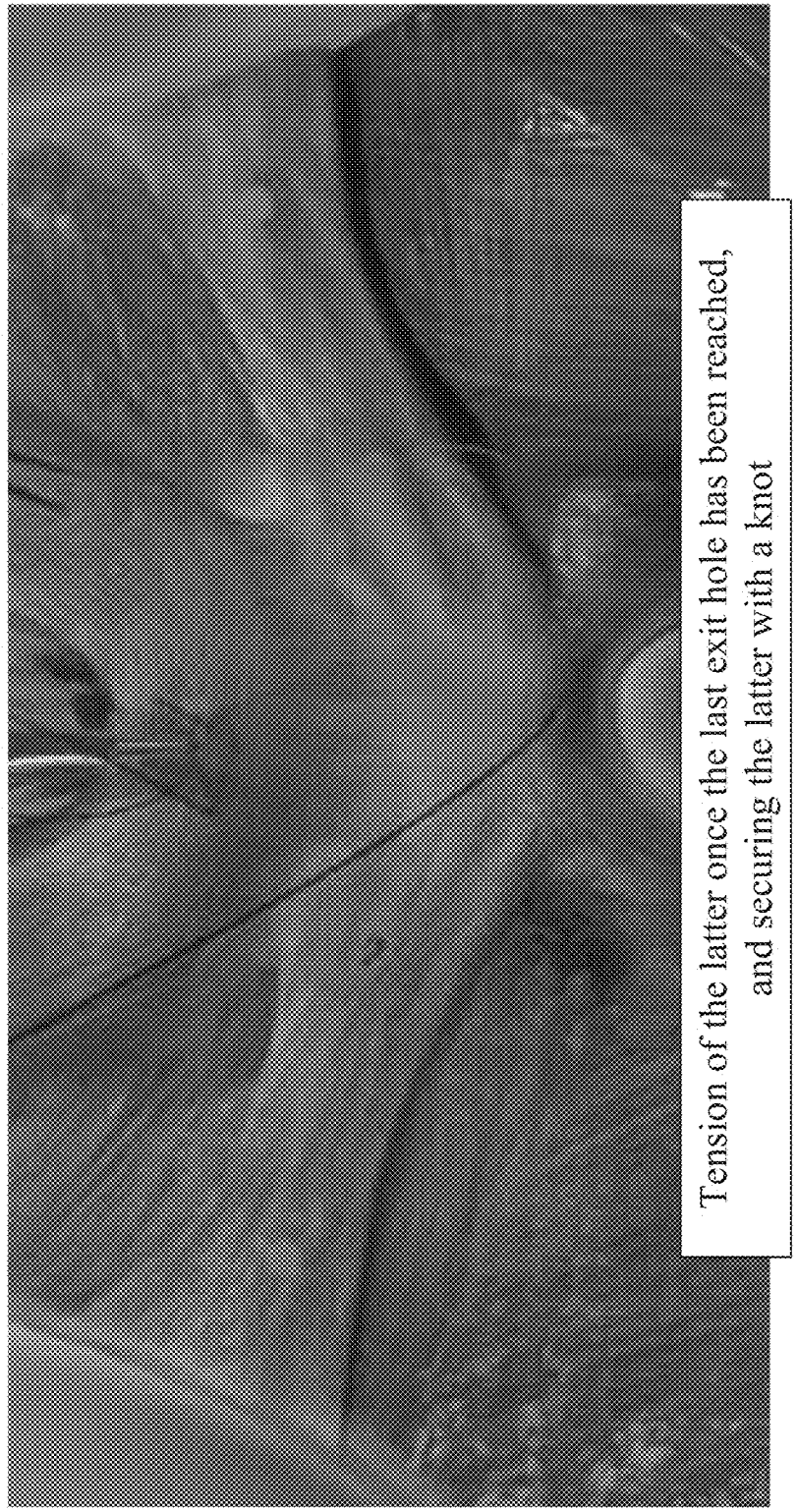
Figure 44:
Figure 45:
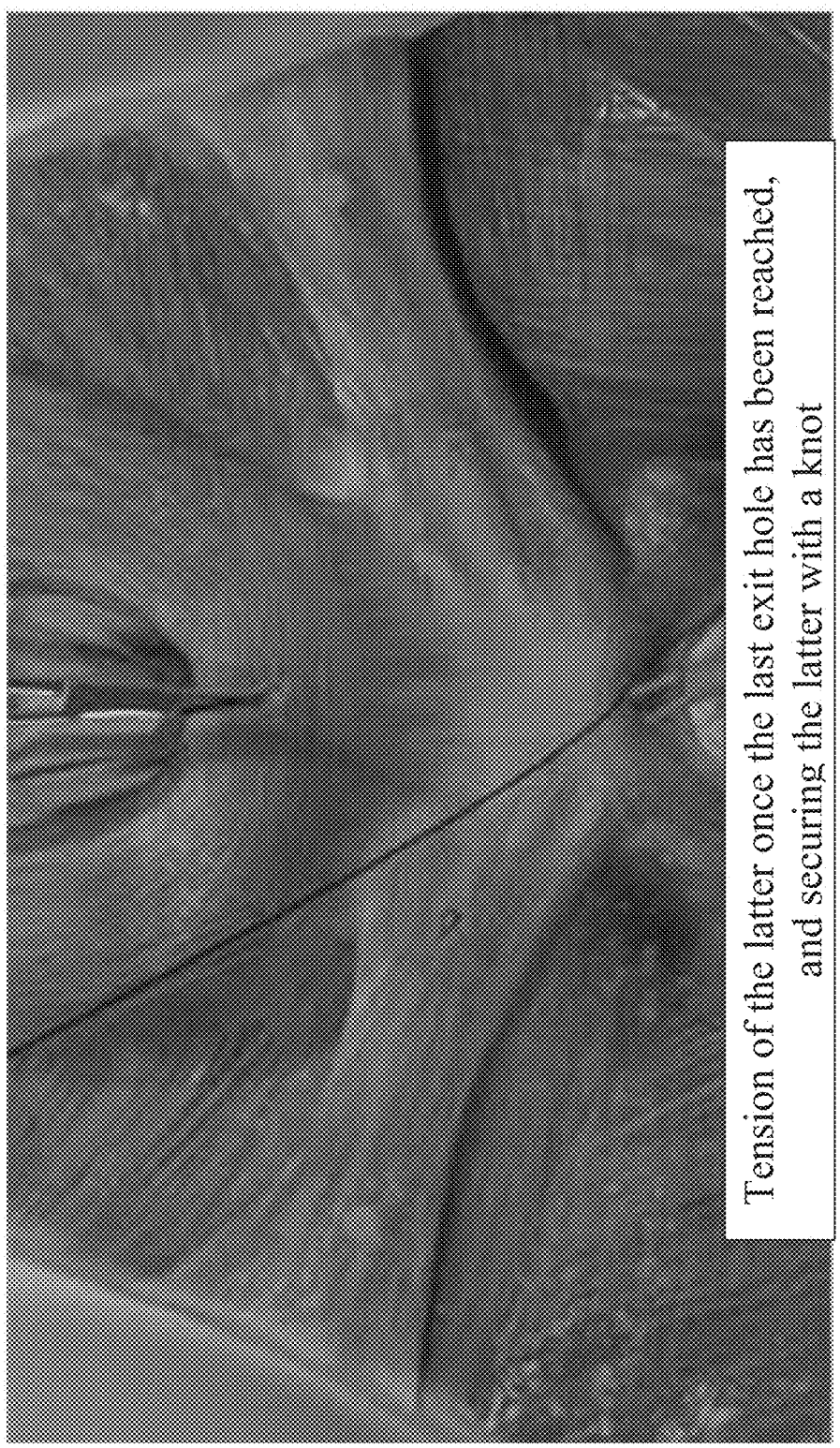
Figure 46:
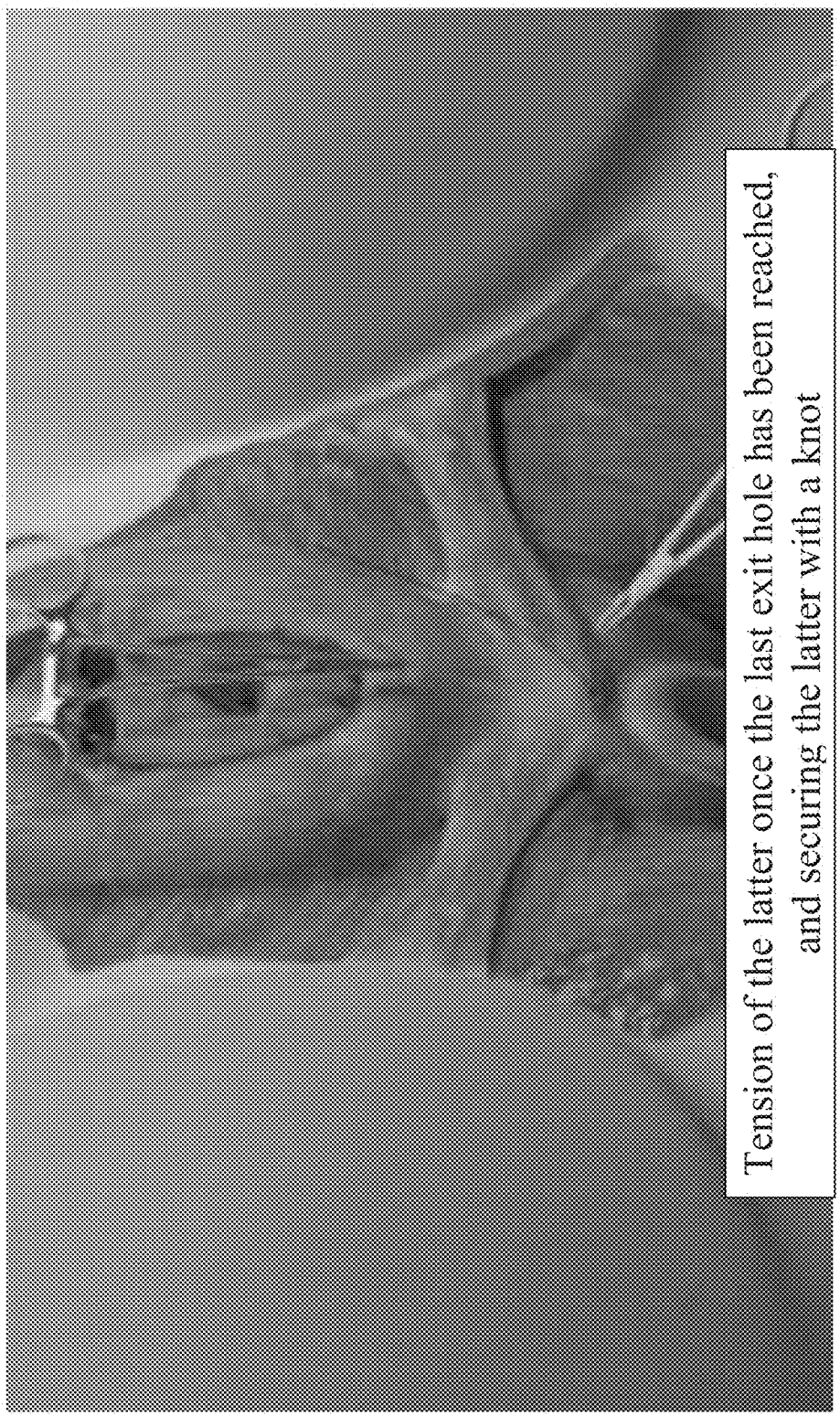
FIG. 46 shows the complete emergence of the vaginal suture on the median distal cut, located on the median raphe (body of the perineum) in the same hole in which the right half-length previously came out; this is followed by the next tensioning of the suture and tightening with a simple forehand, backhand, forehand triple knot.
Figure 47:
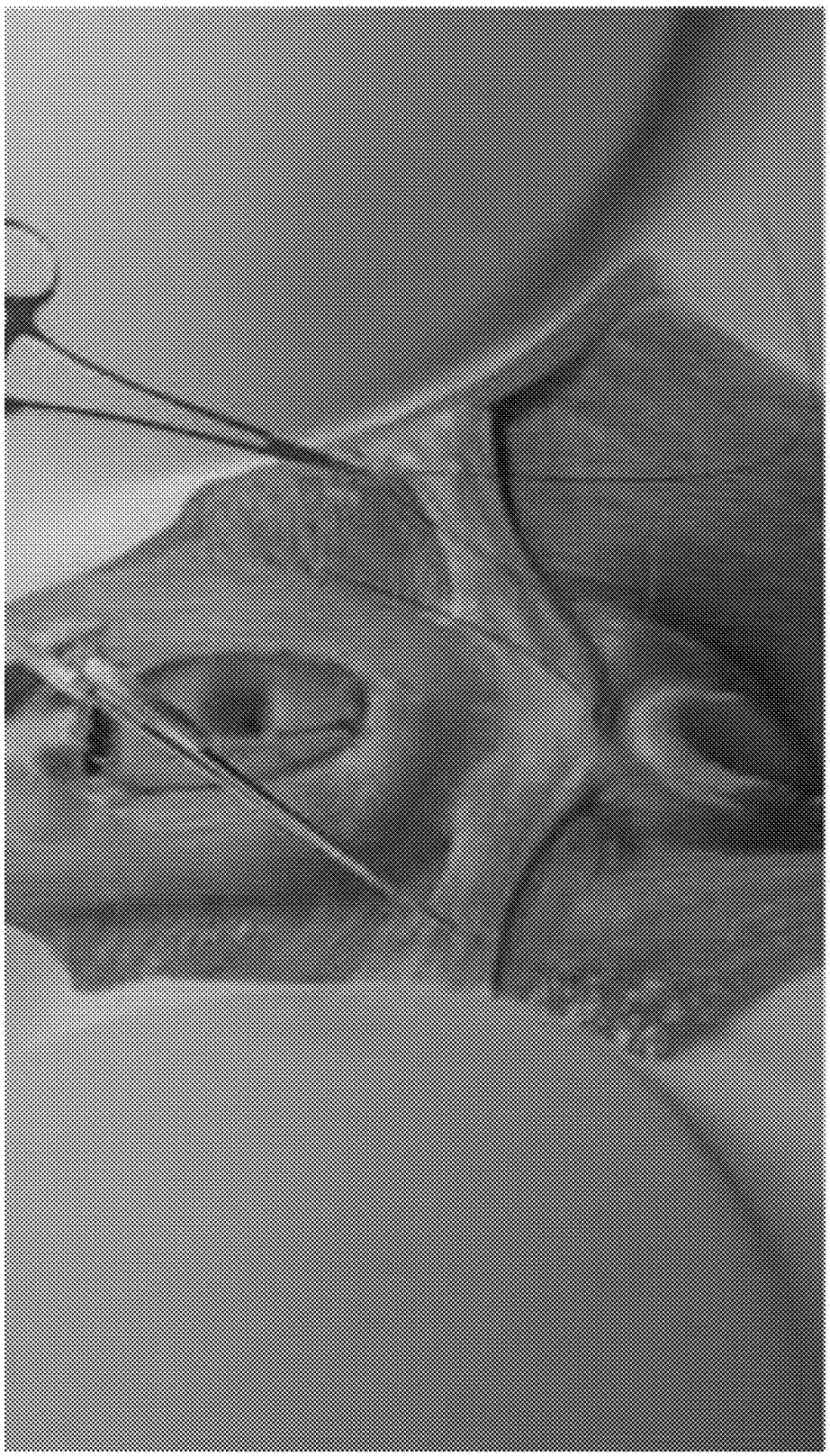
FIG. 47 shows the same procedure for the introduction of the second vaginal suture: the only difference is that the procedure starts now with the introduction of the suture from the "distal" midpoint, then emerging from the right and left transverse external cuts, located at about 1.5/2 cm from the insertion of the transverse muscle of the perineum on the ipsilateral ischial tuberosity.

Once the surgical field has been prepared (FIGS. 27 and 28), and after the sterilization thereof (FIG. 29), the possible introduction of the vaginal catheter (FIG. 30), of a buffer (swab) into the vagina (FIG. 31) and of the anoscope (FIG. 32), usable for both diagnostic purposes and as a reference element of the front wall of the rectal canal (FIGS. 32 and 33), a locoregional topical or lumbosacral plexus (FIG. 35) or general anesthesia is carried out.

For the local anesthesia, Xylocaine or Carbocaine or Mevipacaina 3% is used, with the addition of 1/50,000 diluted Adrenaline, infiltrating not more than 0.5-0.7 ml, for each single needle insertion.

The guidelines to carry out the surgery with the method described are as follows:
a) overelongated vaginal canal,
b) vaginal ostium with mild or moderate dilatation,
c) iatrogenic or traumatic injury of the perineal muscles,
d) tone of the above-mentioned atrophic or hypotonic muscles of the female perineum due to physiological conditions or ageing,
e) nulliparous or multiparous women who have given birth physiologically or through a piloted delivery with or without episiotomy,
f) menopausal women,
7) women who want to improve their sexual area and intimate life.

It is obviously worth noting that vaginal surgery as any other surgery implies certain risks. Some of these are related to the anesthetic and to the surgical procedure which could result in possible injury or trauma to major blood vessels or nerve bundles, bleeding, postoperative infections and even to fistula and blood clot formation. However, these risks have an incidence of less than 1%.

Physical-Chemical Features of Usable Suture Threads

The surgical threads for plastic and gynecologic surgery, and for general surgery are well known (Zoltan). The threads can be made of various materials: permanent or absorbable metals, polymers and biological materials. The general physical, biochemical or biological features of the threads (strength, smooth surface, density, bio-inertia, biodegradability, biocompatibility, anallergicity, tolerability, etc.) must be well-known, and in general they are parameters specifically provided by manufacturers. The threads need to be suitable to be possibly well-bondable in knots to suture wounds or to support or reposition the soft tissues and other tissues of the human body, to support or obtain a proper action of lifting or repositioning of dermatochalasis tissues or finally to remodel the soft tissues while restoring or newly forming the three-dimensional morphological contours of the face or of specific areas of the human body (female perineum).

Finally, the above-mentioned vaginal surgical threads do not have to stretch, if not within the tolerance limits of the material which forms the thread.

The suturing and healing mode of traumatic postpartum and episiotomy wounds with restoration of normal anatomical-functional tension in the anatomical insertion region will be carried out with the techniques outlined above and broadly disclosed below.

In general, depending on the purposes, different surgical threads are used (see the International Conference "Gli approcci correnti allo sviluppo dei materiali e degli impianti polimerici di rivestimento effettivo e di sutura"). The metal threads can be made of tantalum, platinum, silver, gold, nickel, etc. The non-metallic threads are made of Laysan, nylon, caprone, polypropylene, vikril, polisorb, etc. Monolithic, monofilament or multifilament threads may be used, either twisted or untwisted, etc. All these surgical threads have a particular feature: they can cross soft tissues such as the skin, hypodermis tissues, muscle fascia, SMAS, etc, over the whole length in one direction and in the opposite one. This great advantage for surgical threads may become a disadvantage during the plastic surgery and aesthetic gynecologic surgery. Indeed, while suturing a wound in an intradermal or subcutaneous manner, it becomes necessary to draw a suture with a continuous suture process to reinforce the ends of the thread at the beginning and at end of the wound. This lengthens the surgery time and it complicated the healing suture process; sometimes, also due to the reinforcing instability of both ends of the wound. There are several known ways to suture a wound: discontinuous, continuous, etc.

For instance, while carrying out a continuous intradermal suture using soft threads, the suture is usually re-sewn, along the line of the wound. In this case, this result in the scar produced corresponding to the maximum possible length, which is obviously undesirable from the aesthetic point of view, and at the same time a smaller scar can be obtained when suturing a wound with a uniform grouping of the skin along the line of the wound. In this case, with the use of classic soft threads (not barbed like the thread used herein), it is impossible to obtain a uniform corrugation of the wound over its whole length: the skin will be better grouped at the ends, while it will be more released close to the central part; therefore, a necrosis of more grouped tissues can occur and a scar with unpleasant aspect can be highlighted.

Instead, the use of these barbed threads with spatial stereotactic geometry, as shown in this invention, therefore with unidirectional and bidirectional penetration, if necessary, through the tissues allows a uniform juxtaposition of the tissues to be obtained along the wound without corrugation, with distribution of the sealing force embodied by the different types of loops mentioned above, along its whole elongation, with full respect for the normal functional physiology of the crossed tissues, and in specific cases, it also allows to obtain a smaller and good-looking scar, which is of fundamental importance in plastic and gynecologic surgery.

Concluding, the use of the above-described method implies its use for the vulva, the vaginal ostium, the vagina and the female perineum and its marginal areas, for toning up or for surgically reducing them, or for solving the prolapses of the anatomical areas mentioned with closed, end-to-end anastomosis, thus repositioning them in the locations where they were before the iatrogenic and/or traumatic injuries displaced and moved them away from their correct anatomical-functional position. Therefore the problems of plastic surgery, dermatologic surgery, cosmetic and gynecologic surgery, related and specific of feminine sexuality, are solved using our surgical thread in the anatomical skin areas of vulva, vagina, vaginal ostium and female perineum, and in the surrounding areas.

The vaginal suture thread of the invention can be designed and made of non-resorbable or resorbable polymeric, biological or synthesized material, but it must have over its whole length, in specific geometric sequences as already previously documented, protrusions of multi-faceted shape (like a barb), properly sloped and suitably oriented in the opposite direction with respect to the midpoint (P.M.), so as to oppose the traction of the thread exerted on both ends.

The same applies to the anal suture which, despite having the same parameter features of the vaginal suture, differs in terms of length (it is longer) and anatomical application region (Anal Triangle). It is the purpose of this suture to solve and/or reduce the anal prolapse and/or increase the wall tension of the anal sphincter.

REFERENCES

1) Patent DE 4302895 C2, A6IL 17100, published on 04, Sep. 1994
2) Ya.Zoltan "Operational technique and conditions of optimum healing of a wound", Medicine, Budapest, 1977, pp. 44 47, 58 63, 90 91.
3) Materials of the International Conference "Gli approcci correnti allo sviluppo del rivestimento effettivo, dei materiali chirurgici e degli impianti polimerici", 1995, Mosca, The Institute of Surgery, pp. 314 316, 337 340.
4) U.S. Pat. No. 5,374,268 A1, 20, Dec. 1994
5) GB 1506362 A1, 05, Apr. 1978
6) U.S. Pat. No. 4,069,825 A1, 24, Jan. 1978
7) EP 0428253 A1, 22, May 1991

The invention claimed is:

1. A surgical method to perform mini-invasive vaginal ostium plastic surgery and anal tightening procedures, comprising the steps of:
using at least one barbed cylindrical suture thread wherein, with respect to a midpoint of the suture, the barbs are divided into two groups which oppose or diverge from each other, sharp ends of said barbs being inclined in the direction of said midpoint or in the direction of the respective ends, so as to oppose the traction of said suture thread exerted on both ends, each end of said suture thread being provided with a needle;
by using a dermal punch, preparing at least one insertion cut and at least one emergence cut made in the working plane of the female perineum, wherein at least one of said insertion cut and emergence cut is located on the median raphe or central body of the perineum and the other of said insertion cut and emergence cut is located on the superficial transverse muscle on the right side or left side thereof;
introducing said suture thread by inserting the two needles placed at its ends, at different times, into the same insertion cut, in order to emerge from the same emergence cut, thus completing a path in different anatomical planes of the female perineum, so as to affect both surface and deep anatomical planes of the female perineum in order for the suture thread barbs to provide the soft tissue, the corpora cavernosa and the muscle bundles of the different vaginal, vulvar and perineal planes—crossed during travel of the needles and suture in the path—aggregation and support in a specific direction, by using, a loop technique, wherein each loop obtained in the loop technique are one of the group of ring shape, triangular shape, quadrangular shape, and polyhedron shape; and
tying together the two ends of the at least one suture once they have emerged from the same emergence cut, then closing the loop with i) a single simple forehand, backhand suture knot, or ii) with multiple knots.

2. The surgical method according to claim 1, wherein, the two needles comprise a left needle and a right needle, and in the introducing step, the loop technique is a single loop technique, and
using the single loop technique, one of the insertion cut and emergence cut is a first cut (A) made at the median raphe or central body of the perineum (RF), close to the lower fork of the vaginal ostium (OV), and the other one of the insertion cut and emergence cut is a second cut (C) or (B) made to be located on the superficial transverse muscle on the right side or left side, respectively, where both the right and left needles at the single suture ends are indifferently introduced either from the first cut (A) or the second cut (C) or (B), to then emerge from the second cut (C) or (B) or the first cut (A).

3. The method of claim 2, wherein the at least one barbed cylindrical suture thread includes converging barbs that are spirally distributed along the suture surface so as to be in sequence on four generatrices angularly spaced apart by 90°.

4. The surgical method according to claim 1, wherein,
the two needles attached to said suture thread comprise a left needle and a right needle, and
in the introducing step, the loop technique is a quadrangular loop with at least one of a knotted cranial cut and a caudal cut, and the at least one insertion cut comprises two insertion cuts (A, D) and the at least one emergence cut comprises two emergence cuts (B, C) located on right and left oblique axes (B, C) respectively,
where the right needle and the left needle of the suture thread are introduced starting from a first one of the two insertion cuts (A, D) and then:
i) the right needle of the suture thread emerges from a first one of the emergence cuts (B, C), and then reenters in the same first one of the emergence cuts (B, C) to emerge from a second one of the emergence cuts (C, B),
wherein the right needle then reenters into the same second one of the emergence cuts (C, B) in order to next emerge from a second one of the insertion cuts (D, A), and
ii) the left needle of the suture thread emerges from the second one of the emergence cuts (C, B), and then reenters into the same second one of the emergence cuts (C, B) to emerge from a first one of the emergence cuts (B, C),
wherein the left needle then reenters the first one of the emergence cuts (B, C) in order to next emerge from the second one of the insertion cuts (D, A),
thus completing the path in different anatomical planes of the female perineum, and
after the right needle emerges from the second one of the insertion cuts (D, A) and the left needle emerges from the second one of the insertion cuts (D, A), a suture knot with multiple simple forehand, backhand suture parts is made.

5. The surgical method according to claim 1, wherein,
the two needles attached to said suture thread comprises a right needle and a left needle,
in the introducing step, the loop technique is a quadrangular double loop with knotted cranial and/or caudal cut, and
the at least one insertion cut comprises two insertions cuts (A1, D), and the at least one emergence cut comprises four emergence cuts (B, C, F, E) located on right oblique axes (B, C, F, E), and four further emergence cuts (B2, C2, F2, E2) located on left oblique axes (B2, C2, F2, E2) respectively,
wherein the right and left needles of the suture thread are introduced starting from a first one of the two insertion cuts (A1, D), indifferently, and
i) the right needle of the suture thread emerges from a first one of the emergence cuts (B), then the right needle reenters into the same first one of the emergence cuts (B) to next emerge from the a second one of the emergence cuts (C), the right needle reenters the same second one of the emergence cuts (C) in order to next emerge from a third one of the emergence cuts (F) and then the right needle enters into said third one of the emergence cuts (F) to emerge from a fourth one of the emergence cuts (E), wherein the right needle reenters into the fourth one of the emergence cuts (E) in order to next emerge from a second one of the insertion cuts (D, A1) and
ii) the left needle of the suture thread emerges from the first one of the further emergence cuts (B2), then the left needle reenters into the same first one of the further emergence cuts (B2) to next emerge from a second one of the further emergence cuts (C2), the left needle then reenters in the same second one of the further emergence cuts (C2) in order to next emerge from a third one of the further emergence cuts (F2), wherein the left needle reenters the third one of the further emergence cuts (F2) in order to emerge from a fourth one of the further emergence cuts (E2), wherein the left needle reenters into the fourth one of the further emergence cuts (E2) in order to next emerge from the second one of the insertions cuts (D, A1),
thus completing the path in different anatomical planes of the female perineum, and
after the right needle emerges from the second one of the insertion cuts (D, A1) and the left needle emerges from the second one of the insertion cuts (D, A1), a suture knot with multiple simple forehand, backhand suture parts is made.

6. The method of claim 1, wherein the at least one barbed cylindrical suture thread includes converging barbs that are spirally distributed along the suture surface so as to be in sequence on four generatrices angularly spaced apart by 90°.

* * * * *